US012025611B2

(12) United States Patent
Betts-LaCroix

(10) Patent No.: US 12,025,611 B2
(45) Date of Patent: Jul. 2, 2024

(54) METHODS OF PERFORMING ANIMAL RESEARCH

(71) Applicant: Recursion Pharmaceuticals, Inc., Salt Lake City, UT (US)

(72) Inventor: Jonathan Betts-LaCroix, San Mateo, CA (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 1571 days.

(21) Appl. No.: 16/208,261

(22) Filed: Dec. 3, 2018

(65) Prior Publication Data

US 2020/0173982 A1 Jun. 4, 2020

(51) Int. Cl.
*C12M 3/00* (2006.01)
*A61B 5/00* (2006.01)
*A61B 5/145* (2006.01)
*A61B 5/1455* (2006.01)
*A61B 5/1477* (2006.01)
*A61M 1/34* (2006.01)
*A61M 1/38* (2006.01)
*B01L 3/00* (2006.01)
*C12N 5/00* (2006.01)
*G01N 33/50* (2006.01)
*G01N 33/53* (2006.01)

(52) U.S. Cl.
CPC ..... *G01N 33/5005* (2013.01); *A61B 5/14525* (2013.01); *A61B 5/14528* (2013.01); *A61B 5/14539* (2013.01); *A61B 5/1455* (2013.01); *A61B 5/1477* (2013.01); *A61B 5/4845* (2013.01); *A61B 5/4848* (2013.01); *A61M 1/34* (2013.01); *A61M 1/38* (2013.01); *C12N 5/0068* (2013.01); *G01N 33/5302* (2013.01); *A61B 2503/40* (2013.01); *A61B 2503/42* (2013.01)

(58) Field of Classification Search
CPC ....... C12M 23/34; C12M 23/20; C12M 23/16
See application file for complete search history.

(56) References Cited

U.S. PATENT DOCUMENTS

| 5,486,457 | A | 1/1996 | Butler et al. |
| 2005/0033133 | A1 | 2/2005 | Kraft |
| 2012/0085648 | A1 | 4/2012 | Kartalov et al. |
| 2014/0308688 | A1* | 10/2014 | Grego .................... C12M 21/08 435/7.92 |
| 2015/0004077 | A1 | 1/2015 | Wikswo et al. |
| 2016/0326477 | A1* | 11/2016 | Fernandez-Alcon ........................ B01D 63/081 |
| 2017/0009192 | A1* | 1/2017 | Peralta Uroz .......... C12M 25/04 |

OTHER PUBLICATIONS

Co-pending U.S. Appl. No. 16/208,233, filed Dec. 3, 2018.
U.S. Appl. No. 16/208,233, Final Office Action mailed Oct. 31, 2022, 14 pages.
U.S. Appl. No. 16/208,233, Non-Final Office Action mailed Apr. 15, 2022, 16 pages.

* cited by examiner

*Primary Examiner* — Nathan A Bowers
(74) *Attorney, Agent, or Firm* — Keller Precce PLLC

(57) ABSTRACT

Disclosed herein are devices, systems and methods for performing cell culture using animal-chip hybrids. A cell culture device may comprise a fluid channel portion having a first port at a first end and a second port at a second end, and a first compartment for culturing cells. A continuous or intermittent perfusion of blood from an animal subject may enter the cell culture device at the first port and exit the cell culture device at the second port.

20 Claims, 9 Drawing Sheets

METHODS OF PERFORMING ANIMAL RESEARCH

BACKGROUND

During the process of cell culture, a collection of human, animal, or bacterial cells are typically cultured in an in vitro medium. Culturing such cells using a hybrid in vitro-in vivo system comprising an animal-chip hybrid with perfusion of animal blood may improve cell culture.

SUMMARY

Devices, systems and methods are disclosed for performing cell culture using an animal-chip hybrid with perfusion of animal blood.

In an aspect, the present disclosure provides a method for processing or analyzing biological material, the method comprising: providing a device comprising (1) a housing comprising (i) a channel having an inlet and an outlet, wherein the inlet and the outlet of the channel are configured to bring the channel in fluid communication with a circulatory system of a subject when the housing is secured to the subject, and (ii) a compartment fluidly connected to the channel, which compartment is configured to process or analyze the biological material; and (2) a fastener configured to secure the housing to a body of the subject; and using the fastener to secure the housing to the body of the subject.

In some embodiments, the method further comprises bringing the inlet and the outlet in fluid communication with the circulatory system of the subject. In some embodiments, the biological material is subjected to fluid from the circulatory system of the subject. In some embodiments, the biological material is subjected to the fluid in a continuous manner. In some embodiments, the biological material is subjected to the fluid in an intermittent manner. In some embodiments, the device further comprises a semi-permeable layer positioned between the channel portion and the compartment. In some embodiments, the semi-permeable layer is cell-selective. In some embodiments, the semi-permeable layer is size-selective. In some embodiments, the semi-permeable layer is a layer of cells, a lipid bilayer, a polymer gel, or a microporous membrane. In some embodiments, the layer of cells is selected from the group consisting of epithelial cells, endothelial cells, vascular endothelial cells, pericytes, astrocytes, a multi-cell-type model of the blood-CSF barrier, choroid plexus epithelial cells, epiplexus immune cells, a multi-cell-type model of the blood-brain barrier, or any combinations thereof.

In some embodiments, the microporous membrane comprises a polymer selected from the group consisting of polyethylene terephthalate, polystyrene, cellulose acetate, cellulose nitrate, nylon, glass fiber, nylon, polyethersulfone (PES), polypropylene (PP), polytetrafluoroethylene (PTFE), hydrophilic PTFE, polyvinylidene fluoride (PVDF), hydrophilic PVDF, cellulose ester, polysulfone, etched polycarbonate, collagen, and regenerated cellulose.

In some embodiments, the device is fabricated from a polymer. In some embodiments, the polymer is selected from the group consisting of polydimethylsiloxane, a thermoset polyester, a thermoplastic polymer, polystyrene, polycarbonate, poly-methyl methacrylate (PMMA), poly-ethylene glycol diacrylate (PEGDA), perfluoroalkoxy alkane, fluorinated ethylene propylene, photocurable perfluoropolyether, polyfluoropolyether diol methacrylate, poly(N-isopropylacrylamide) (PNIPAAm), and polyurethane (PU).

In some embodiments, the device further comprises two or more compartments. In some embodiments, the two or more compartments are arranged in a linear fashion. In some embodiments, the two or more compartments are arranged in an array. In some embodiments, each compartment comprises a coating. In some embodiments, the coating is a hydrophilic coating. In some embodiments, the hydrophilic coating is selected from the group consisting of a constituent of a natural extracellular matrix of an animal tissue, a laminin protein, collagen-type IV, fibronectin, poly-L-lysine, and poly-D-lysine. In some embodiments, the coating further comprises an antibody. In some embodiments, the antibody binds specifically to a cadherin, an integrin, a C-type lectin-like domain (CTLD), a proteoglycan, or any combinations thereof.

In some embodiments, the device further comprises two or more semi-permeable layers positioned between each of the two or more compartments. In some embodiments, each compartment further comprises a matrix. In some embodiments, the device further comprises two or more inlets. In some embodiments, the device further comprises two or more outlets. In some embodiments, the subject is a mammal. In some embodiments, the mammal is an animal or a human. In some embodiments, the animal is selected from the group consisting of a mouse, a rat, a hamster, a guinea pig, a rabbit, a pig, a dog, a cat, a bird, a fish, a monkey. In some embodiments, the monkey is a chimpanzee. In some embodiments, the biological material is a cell or a xenograft.

In some embodiments, the cell is a human cell, an animal cell or a bacterial cell. In some embodiments, the cell is selected from the group consisting of endothelial cells, epithelial cells, red blood cells, white blood cells (leukocytes), monocytes, platelets, fibroblasts, neuronal cells, primary cells, stem cells, or tumor-derived cells.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
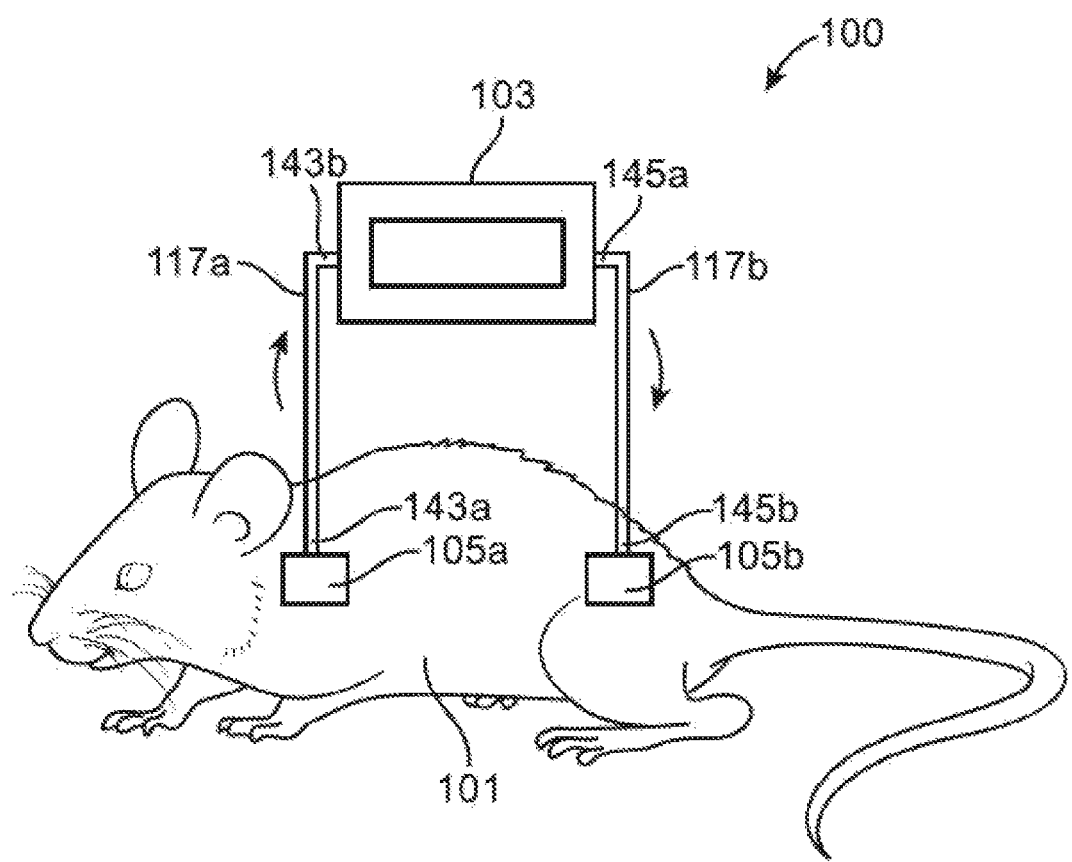
FIG. 1 illustrates an example of an animal-chip hybrid system comprising an animal subject and a cell culture device, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Devices, systems and methods are provided for performing cell culture using an animal-chip hybrid with perfusion of animal blood. A cell culture device may comprise a fluid channel portion having a first port at a first end and a second port at a second end, and a compartment for culturing cells. A continuous or intermittent perfusion of blood from an animal subject may enter the cell culture device at the first port and exit the cell culture device at the second port.

Definitions

Unless otherwise defined, all technical and scientific terms used herein have the same meaning as commonly understood by one of ordinary skill in the art to which this invention belongs. The terminology used herein is for the purpose of describing particular cases only and is not intended to be limiting.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "about" or "approximately" refers to an amount that is near the stated amount by about 10%, 5%, or 1%, including increments therein. For example, "about" or "approximately" can mean a range including the particular value and ranging from 10% below that particular value and spanning to 10% above that particular value.

The terms "subject," "individual," "host," "donor," and "patient" are used interchangeably herein to refer to a vertebrate, for example, a mammal. Mammals include, but are not limited to, murine, simians, humans, farm animals, sport animals, and pets. Tissues, cells, and their progeny of a biological entity obtained in vivo or cultured in vitro are also encompassed. Designation as a "subject," "individual," "host," "donor," or "patient" does not necessarily entail supervision of a medical professional.

The term "biological material," as used herein, generally refers to any material that may serve a chemical or biological function. Biological material may be biologically functional cells, tissue, or functional tissue, which may be a biological structure that is capable of serving, or serving, a biomechanical or biological function. Biologically functional tissue may comprise cells that are within diffusion distance from each other, comprises at least one cell type wherein each cell is within diffusion distance of a capillary or vascular network component, facilitates and/or inhibits the fulfillment of protein function, or any combination thereof. Biologically functional tissue may be at least a portion of tissue or an organ, such as a vital organ. In some examples, the biological material may be used for drug development, such as, for example, screening multiple cells or tissue with different therapeutic agents.

Biological material may include a matrix, such as a polymeric matrix, including one or more other types of material, such as cells. Biological material may be in various shapes, sizes or configurations.

As used herein, the terms "cell culture device," "chip," and "cell culture chip," are used interchangeably herein to refer to any type of cell culture device described elsewhere herein (e.g., cell culture device 103, elastic cell culture device 104, and plasma exchange cell culture device 109).

Cell Culture

Cell culture generally refers to the maintenance and growth of cells in a controlled laboratory (in vitro) environment. Populations of cells (e.g., cell colonies) in a cell culture may be cultured, maintained, analyzed, and experimented with at macroscale (e.g., bulk cell culture systems) or microscale volumes (e.g., microfluidic cell culture systems). Cell culture on a macroscale or on a microfluidic scale is essential to a broad range of studies in the life sciences, including cellular analysis, cellular microenvironment, cellular secretion, chemotaxis, apoptosis, vascular function, neuron culture and development, single cell resolution metabolomics, population transcriptomics, lab-on-chip platforms, large-scale integration and biological automation, micro total analysis systems, drug research, cellular separations, stem cell biology, system biology, bioreactors, three dimensional cell culture, tissue engineering, and organ-on-chip development.

Conventional cell culture techniques over the past few decades have generally comprised growing cell colonies in vitro in homogeneous culture media contained in large containers or chambers (e.g., flasks or dishes) of predefined chemical and physical properties (e.g., glass or polystyrene). These artificial growth conditions may introduce biases into cell growth cycles, since in vivo cells generally respond to their surrounding microenvironment. Thus, there is a need for a hybrid in vitro-in vivo cell culture device that retains the flexibility of an in vitro cell culture device while maintaining a relatively natural in vivo microenvironment for the cell colonies.

Performing cell culture using a hybrid in vitro-in vivo cell culture device may be advantageous in several ways, including the ability to (i) more closely mimic a cell's natural macro and microenvironment, (ii) study a small number or single cells in high temporal and/or spatial resolution, (iii) perform continuous perfusion culture over longer periods, (iv) directly couple cell cultures to downstream analysis systems, (v) more strictly maintain and predict cell culture conditions (e.g., restricting contamination through minimizing handling steps), (vi) perform controlled co-culture, and/or (vii) perform high-throughput scalable experimentation through parallelization. For example, continuous perfusion cell culture using a hybrid in vitro-in vivo cell culture device can be performed using a small amount of reagents, reduced contamination risk, and efficient high throughput experimentation. A hybrid in vitro-in vivo cell culture device can also be used to perform cell assays, e.g., using cell colonies to test the effects of chemicals such as for drug screening (e.g., using constant chemical doses or chemical gradients). Conventional cell assays typically involve significant resources in terms of laboratory equipment, consumable reagents, and labor. The present disclosure provides devices, methods, and systems for processing or analyzing a biological material. In an aspect, a device for processing or analyzing a biological material, comprises a housing comprising (i) a channel having an inlet and an outlet, wherein the inlet and the outlet of the channel are configured to bring the channel in fluid communication with a circulatory system of a subject when the housing is secured to the subject, and (ii) a compartment fluidly connected to the channel, which compartment is configured to process or analyze the biological material; and a fastener configured to secure the housing to a body of the subject.

Device

In an aspect, a device for processing or analyzing a biological material comprises a housing. The housing may comprise a channel having an inlet and an outlet. The inlet and the outlet of the channel may be configured to bring the channel in fluid communication with a circulatory system of a subject when the housing is secured to the subject. The housing may comprise a compartment fluidly connected to the channel. The compartment may be configured to process or analyze the biological material. The device may comprise a fastener configured to secure the housing to a body of the subject.

The device may be fabricated from a polymer. The polymer may be selected from the group consisting of polydimethylsiloxane, a thermoset polyester, a thermoplastic polymer, polystyrene, polycarbonate, poly-methyl methacrylate (PMMA), poly-ethylene glycol diacrylate (PEGDA), perfluoroalkoxy alkane, fluorinated ethylene propylene, photocurable perfluoropolyether, polyfluoropolyether diol methacrylate, poly(N-isopropylacrylamide) (PNIPAAm), and polyurethane (PU). The device may further comprise two or more inlets. The device may further comprise two or more outlets.

Fluid Channel

The cell culture device of the hybrid in vitro-in vivo system may comprise a fluid channel portion ("fluid channel") (not shown in FIGS. 1-9). The fluid channel may be located within the cell culture device. The fluid channel may have a first port at a first end and a second port at a second end. The first port at the first end may allow a fluid to enter the device (e.g., into the fluid channel portion of the device). The second port at the second end may allow a fluid to exit the device (e.g., out of the fluid channel portion of the device). The fluid may be a bodily fluid (e.g., blood or plasma). Alternatively, the fluid may be a cell medium fluid suitable for performing cell culture.

The hybrid in vitro-in vivo cell culture device may allow a perfusion of bodily fluid (e.g., blood) from an animal subject to enter, flow through, and exit the cell culture device 103, e.g., by entering the device at the first port and exiting the device at the second port. Such perfusion of blood may be performed in a continuous manner (e.g., with continuous fluid flow). Alternatively, such perfusion of blood may be performed in an intermittent manner (e.g., with alternating periods of active fluid flow and no fluid flow). Such intermittent perfusion of blood may be controlled, e.g., by a system comprising a pump and/or valves.

The fluid channel may comprise one or more dimensions. For example, a fluid channel may have a cylindrical shape comprising a diameter and a height. Such a cylindrical fluid channel may have a diameter of, for example, no more than about 1 mm, no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm. Such a cylindrical fluid channel may have a height of, for example, no more than about 1 mm, no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

In some cases, a fluid channel may comprise a microfluidic channel having a cylindrical shape comprising a diameter and a height. Such a cylindrical microfluidic channel may have a diameter of, for example, no more than about 10 micrometers or microns (μm), no more than about 20 μm, no more than about 30 μm, no more than about 40 μm, no more than about 50 μm, no more than about 60 μm, no more than about 70 μm, no more than about 80 μm, no more than about 90 μm, no more than about 100 μm, no more than about 150 μm, no more than about 200 μm, no more than about 250 μm, no more than about 300 μm, no more than about 350 μm, no more than about 400 μm, no more than about 450 μm, no more than about 500 μm, no more than about 550 μm, no more than about 600 μm, no more than about 650 μm, no more than about 700 μm, no more than about 750 μm, no more than about 800 μm, no more than about 850 μm, no more than about 900 μm, no more than about 950 μm, or no more than about 1,000 μm. Such a cylindrical microfluidic channel may have a height of, for example, no more than about 10 micrometers or microns (μm), no more than about 20 μm, no more than about 30 μm, no more than about 40 μm, no more than about 50 μm, no more than about 60 μm, no more than about 70 μm, no more than about 80 μm, no more than about 90 μm, no more than about 100 μm, no more than about 150 μm, no more than about 200 μm, no more than about 250 μm, no more than about 300 μm, no more than about 350 μm, no more than about 400 μm, no more than about 450 μm, no more than about 500 μm, no more than about 550 μm, no more than about 600 μm, no more than about 650 μm, no more than about 700 μm, no more than about 750 μm, no more than about 800 μm, no more than about 850 μm, no more than about 900 μm, no more than about 950 μm, or no more than about 1,000 μm.

As another example, a fluid channel may have a rectangular shape comprising three dimensions (e.g., a length, a width, and a height). Such a rectangular fluid channel may have as any of its dimensions, for example, no more than about 1 mm, no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

In some cases, a fluid channel may comprise a microfluidic channel having a rectangular shape comprising three dimensions (e.g., a length, a width, and a height). Such a rectangular microfluidic channel may have as any of its dimensions, for example, no more than about 10 micrometers or microns (μm), no more than about 20 μm, no more than about 30 μm, no more than about 40 μm, no more than about 50 μm, no more than about 60 μm, no more than about 70 μm, no more than about 80 μm, no more than about 90 μm, no more than about 100 μm, no more than about 150 μm, no more than about 200 μm, no more than about 250 μm, no more than about 300 μm, no more than about 350 μm, no more than about 400 μm, no more than about 450 μm, no more than about 500 μm, no more than about 550 μm, no more than about 600 μm, no more than about 650 μm, no more than about 700 μm, no more than about 750 μm, no more than about 800 μm, no more than about 850 μm, no more than about 900 μm, no more than about 950 μm, or no more than about 1,000 μm.

As another example, a fluid channel may have a spherical or hemispherical shape comprising a radius. Such a spherical or hemispherical fluid channel may have a radius of, for example, no more than about 1 mm, no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 25 mm, no more than about 30 mm, no more than about 35 mm, no more than about 40 mm, no more than about 45 mm, no more than about 50 mm, no more than about 55 mm, no more than about 60 mm, no more than about 65 mm, no more than about 70 mm, no more than about 75 mm, no more than about 80 mm, no more than about 85 mm, no more than about 90 mm, no more than about 95 mm, no more than about 100 mm, no more than about 105 mm, no more than about 110 mm, no more than about 115 mm, no more than about 120 mm, no more than about 125 mm, no more than about 130 mm, no more than about 135 mm, no more than about 140 mm, no more than about 145 mm, or no more than about 150 mm.

In some cases, a fluid channel may comprise a microfluidic channel having a spherical or hemispherical shape comprising a radius. Such a spherical or hemispherical microfluidic channel may have a radius of, for example, no more than about 10 micrometers or microns (μm), no more than about 20 μm, no more than about 30 μm, no more than about 40 μm, no more than about 50 μm, no more than about 60 μm, no more than about 70 μm, no more than about 80 μm, no more than about 90 μm, no more than about 100 μm, no more than about 150 μm, no more than about 200 μm, no more than about 250 μm, no more than about 300 μm, no more than about 350 μm, no more than about 400 μm, no more than about 450 μm, no more than about 500 μm, no more than about 550 μm, no more than about 600 μm, no more than about 650 μm, no more than about 700 μm, no more than about 750 μm, no more than about 800 μm, no more than about 850 µm, no more than about 900 µm, no more than about 950 µm, or no more than about 1,000 µm.

In a preferred embodiment, the fluid channel is fluidly connected to one or more compartments for culturing cells. The fluid channel may be directly fluidly connected to some or all of the one or more compartments via one or more ports. Alternatively, the fluid channel may be indirectly fluidly connected to some or all of the one or more compartments via one or more pieces of tubing (e.g., intravenous tubing).

Animal Subject

In some embodiments, the animal subject is a rodent or a primate. The animal subject may be a mammal. The animal subject may be a mouse, a rat, a hamster, a guinea pig, a rabbit, a pig, a dog, a cat, a bird, a fish, a monkey, or a chimpanzee.

In some embodiments, one or more ports (e.g., a first port and a second port) of the cell culture device are fluidly connected to a continuous animal infusion system. The hybrid in vitro-in vivo cell culture device may allow a perfusion of bodily fluid (e.g., blood) from an animal subject to enter, flow through, and exit the device, e.g., by entering the device at the first port and exiting the device at the second port. Such perfusion of blood may be performed in a continuous manner (e.g., with continuous fluid flow). Alternatively, such perfusion of blood may be performed in an intermittent manner (e.g., with alternating periods of active fluid flow and no fluid flow). Such intermittent perfusion of blood may be controlled, e.g., by a system comprising a pump and/or valves.

Figure 2:
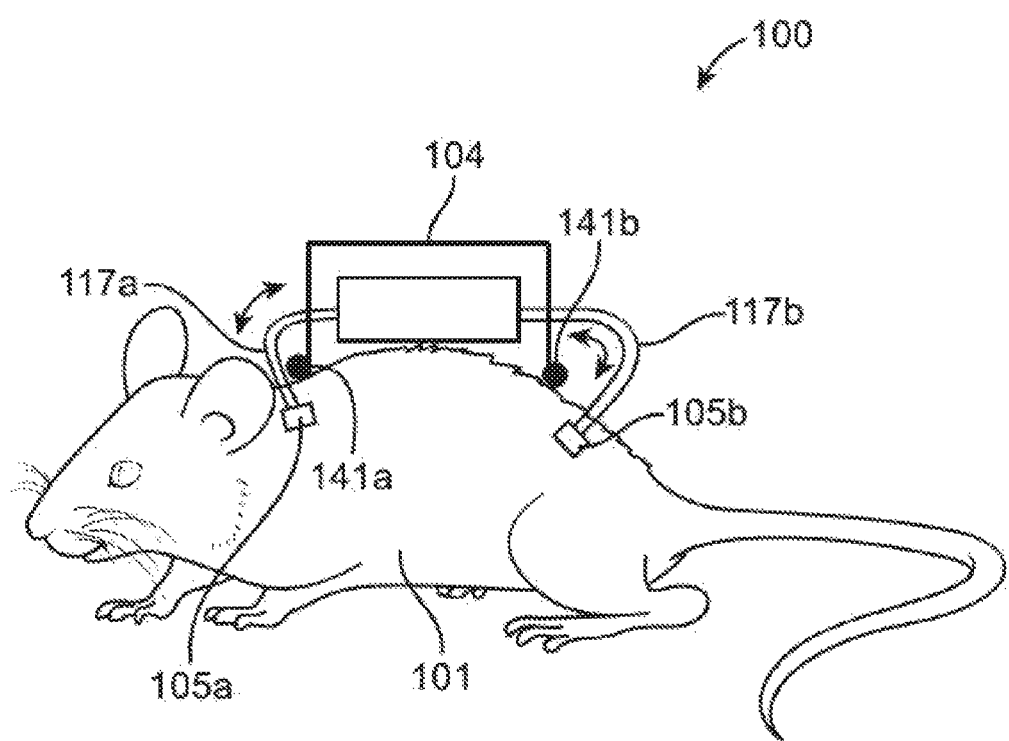
FIG. 2 illustrates an example of an integrated animal-chip hybrid system comprising an animal subject and an elastic cell culture device that is mechanically attached to the animal subject, in accordance with some embodiments.

In some embodiments, the cell culture device is elastic and is mechanically attached to the animal subject, as shown in FIG. 2. The elastic cell culture device may be configured to be mechanically attached to the animal subject, for a number of advantageous purposes, e.g., to allow more natural movements of the animal subject (e.g., continual movement including locomotion and respiration to minimize metabolic stresses on the animal subject), to avoid a distortion of body shape of the animal subject, to induce a distortion of the chip via the mechanical attachment (e.g., for experimental purposes), etc. A variety of attachments may be used to mechanically attach the device to the animal subject, such as glues, adhesives, backing materials coated with an adhesive, tubing, sutures, swivels, tethers, clips, harnesses, meshes, helmets, a harness, a jacket, a patch, or bands. The elastic cell culture device may be mechanically attached to the animal subject via vein and artery portals. In some embodiments, the device is elastic (e.g., comprises an elastic material such as polydimethylsiloxane (PDMS)), such that the device can better adhere to or otherwise be mechanically attached to the animal subject.

Compartment for Culturing Cells

The device may further comprise two or more compartments. The two or more compartments may be arranged in a linear fashion. The two or more compartments may be arranged in an array. The device may further comprise two or more semi-permeable layers between each of the two or more compartments. Each compartment may further comprise a matrix. The matrix may be an extracellular matrix, such as collagen or fibronectin. The matrix may be a polymeric matrix. The matrix may be a hydrogel. The matrix may comprise alginate, hyaluronic acid, agarose, gelatin, poly(lactic-co-glycolic acid), fibrin, chitosan, polyglycolic acid (PGA), polylactic acid, polyethylene oxide, polyethylene glycol, polypropyleneoxide, poly(N-isopropylacrylamide), or any combination thereof.

The hybrid in vitro-in vivo cell culture device may comprise one or more compartments (e.g., cell culture compartments). In some cases, the fluid channel may serve as a compartment for culturing cells or for infusing one or more drugs/toxins. Each of these compartments may be used, for example, for culturing cells (e.g., by infusing cell culture media or nutrients), performing drug assays (e.g., by infusing drugs), and performing toxicity screens (e.g., by infusing potential toxins). For example, the hybrid in vitro-in vivo cell culture device may comprise a first compartment (e.g., for culturing cells). Alternatively, the hybrid in vitro-in vivo cell culture device may comprise a first compartment (e.g., for culturing cells) and a second compartment (e.g., for culturing cells). Alternatively, the hybrid in vitro-in vivo cell culture device may comprise a first compartment (e.g., for culturing cells), a second compartment (e.g., for culturing cells), and a third compartment (e.g., for culturing cells). Alternatively, the hybrid in vitro-in vivo cell culture device may comprise a first compartment (e.g., for culturing cells), a second compartment (e.g., for culturing cells), a third compartment (e.g., for culturing cells), and a fourth compartment (e.g., for culturing cells). Each compartment of the one or more compartments may comprise one or more inlet ports (e.g., through which fluid enters the compartment from the fluid channel) and one or more outlet ports (e.g., through which fluid exits the compartment into the fluid channel). Each of the one or more compartments may be fluidly distinct or separated from each other (e.g., such that local fluid conditions such as infusion of drugs or nutrients is independent across different compartments among the one or more compartments). The one or more compartments may be arranged in a linear or array fashion, as described elsewhere herein.

In some embodiments, any (e.g., some or all) of the one or more compartments for culturing cells of the hybrid in vitro-in vivo cell culture device is fluidly connected to the fluid channel. The fluidic connection between the fluid channel portion and a compartment for culturing cells may allow continuous or intermittent fluid exchange to occur between the fluid channel portion and a compartment for culturing cells. Such continuous or intermittent fluid exchange may allow substantially all or most of a bodily fluid (e.g., blood) to be perfused and to interact with the cells being cultured in a compartment for culturing cells.

The device may selectively restrict some portion of a bodily fluid (e.g., blood) from being perfused and interacting with the cells being cultured in a compartment for culturing cells, while allowing another portion of the bodily fluid (e.g., plasma) to freely perfuse and interact with the cells being cultured in a compartment for culturing cells.

For example, continuous restricted fluid exchange may occur if there is a barrier layer present between the fluid channel portion and a compartment for culturing cells. In some cases, a barrier layer may be present between one or more compartments (e.g., cell culture compartments). Such a barrier layer may selectively restrict or allow portions of a bodily fluid to pass through the barrier layer. For example, a barrier layer may be configured such that all cells may be restricted from pass through the barrier layer but other non-cell entities such as drugs and nutrients may be allowed (unrestricted) to pass through the barrier layer. As another example, a barrier layer may be configured such that all cells larger than a certain size (e.g., diameter) may be restricted from pass through the barrier layer but other cells no larger than the certain size and non-cell entities such as drugs, nutrients, and waste products may be allowed (unrestricted) to pass through the barrier layer. For example, drugs and nutrients may be allowed to pass from the fluid channel portion into a compartment for culturing cells (e.g., for cell assaying and/or cell culturing purposes). As another example, waste products may be allowed to pass from a compartment for culturing cells into the fluid channel portion (e.g., for waste elimination purposes).

Alternatively, the continuous or intermittent fluid exchange may not restrict any portion of a bodily fluid (e.g., blood) from being perfused and interacting with the cells being cultured in a compartment for culturing cells. For example, continuous unrestricted fluid exchange may occur if a layer (e.g., a membrane) is present between the fluid channel portion and a compartment for culturing cells such that the layer allows substantially all or most of the bodily fluid (e.g., blood) to be perfused and interact with the cells being cultured in a compartment for culturing cells.

Each of the one or more compartments for culturing cells may comprise any suitable material for allowing cell culture, such as those typically used in conventional cell culture (e.g., glass or polydimethylsiloxane (PDMS)).

The one or more compartments for culturing cells may comprise a portion with transparent, translucent, and/or fluorescence-blocking optical properties. For example, a transparent portion (e.g., window) may allow visualization of cells by light microscopy or other detecting methods. A compartment for culturing cells may comprise a plurality of individual cell culture chambers, each of which may function as a separate compartment for culturing cells. In a preferred embodiment, the individual cell culture chambers of a cell culture compartment are fluidly connected. Each of the one or more compartments for culturing cells may comprise a glass material suitable for direct cell culturing. Such a glass material may not optimally support cell adhesion due to its hydrophobicity, and as such may require a surface coating to promote cell attachment. A glass material of each of the one or more compartments for culturing cells may be coated with a hydrophilic coating such that the surface of the glass material is adhesive to many or virtually all cell types.

Each compartment may comprise a coating. The coating may be a hydrophilic coating. The hydrophilic coating may be a constituent of a natural extracellular matrix of animal tissue. The constituent of a natural extracellular matrix of animal tissue includes, but is not limited to heparan sulfate, chondroitin sulfate, keratan sulfate, hyaluronic acid, collagen, elastin, fibronectin, laminin, perlecan, and agrin. The hydrophilic coating may be collagen type IV. The hydrophilic coating may be a fibrillar collagen, a facit collagen, a short chain collagen, and/or a basement membrane collagen. The hydrophilic coating may be a fibrillar collagen such as collagen type I, II, III, V, and/or XI. The hydrophilic coating may be a facit collagen such as collagen type IX, XII, and/or XIV. The hydrophilic coating may be a short chain collagen such as collagen type VIII and/or X. The hydrophilic coating may be a basement membrane collagen such as collagen type IV. The hydrophilic coating may be collage type VI, VII, and/or XIII. The hydrophilic coating may be selected from the group consisting of a constituent of a natural extracellular matrix of an animal tissue, a laminin protein, collagen-type IV, fibronectin, poly-L-lysine, and poly-D-lysine.

A compartment for culturing cells may comprise a material with a hydrophilic coating comprising an extracellular matrix coating, such as collagen or fibronectin. A compartment for culturing cells may comprise a material with a hydrophilic coating comprising collagen type IV ("collagen IV"). A material (e.g., glass) coated with such a collagen IV coating may be referred to as a collagen IV substrate. Such a collagen IV substrate may be suitable for performing cell culture on a variety of standard cell lines, such as epithelial, endothelial, nerve, and muscle cells. Alternatively, a compartment for culturing cells may comprise a material with a hydrophilic coating comprising fibronectin. A material (e.g., glass) coated with such a fibronectin coating may be referred to as a fibronectin substrate. Such a fibronectin substrate may be suitable for performing cell culture on neural cells, including glial and neural cells.

Alternatively, a compartment for culturing cells may comprise a material with a hydrophilic coating comprising poly-L-lysine (PLL) or poly-D-lysine (PDL). A material (e.g., glass) coated with such a collagen IV coating may be referred to as a PLL or PDL substrate. Such a PLL or PDL substrate may be suitable for performing cell culture on a variety of standard cell lines, such as neuronal cultures.

Alternatively, the coating may further comprise an antibody. The coating may comprise an antibody that binds to a specific surface protein of a cell of interest (e.g., cardiomyocytes). For example, the coating may comprise an antibody that binds specifically to a cadherin, an integrin, a C-type lectin-like domain (CTLD), a proteoglycan, or any combinations thereof. In an aspect, the present disclosure provides a device for processing or analyzing biological material such as cardiomyocytes. In such a case, the compartment for culturing cells may comprise a coating that further comprises an antibody that binds specifically to a cardiomyocyte marker including, but not limited to cardiomyocyte cadherin. In another example, the cell compartment may be used to cultured endothelial cells. In such a case, the compartment for culturing cells may comprise a coating that further comprises an antibody that binds specifically to an endothelial cell marker including, but not limited to platelet endothelial cell adhesion molecule (PECAM). In yet another example, the cell compartment may comprise a mixture of cells comprising one or more cell types. In such a case, the compartment for culturing cells may comprise a coating that further comprises one or more antibodies that bind specifically to one or more markers that are expressed by the one or more cell types being cultured in the device.

The geometry (e.g., shape and/or thickness) of the cell culture compartment (or alternatively, a cell culture chamber) may influence the circulation of cell culture medium and the physiologically simulated cell and/or tissue growth environment. For example, control over the transport of oxygen and nutrients into the cell culture compartment and the transport of waste elimination out of the cell culture compartment may be precisely controlled or tuned (e.g., to simulate cell growth conditions corresponding to a particular cell type, tissue type, or organ type). As such, the geometry of the cell culture compartments may be selected or precisely controlled (e.g., using soft lithographic or other fabrication techniques).

In some embodiments, a compartment for culturing cells (or alternatively a cell culture chamber) contains an agent to capture or localize cells within the chamber. Such an agent may comprise any suitable two-dimensional or a three-dimensional matrix or scaffold in the cell culture compartment. For example, cells may be cultured in free suspension (e.g., a cell medium), on a surface, or encapsulated in any suitable hydrogel (e.g., alginate) for cell culture. Such encapsulation may be desirable for facilitating ease of removal of cells during or after experiments (e.g., drug or toxicity assays) are performed. In some cases, the agent comprises one or more antibodies attached to one or more surfaces (e.g., a floor, a wall, a ceiling, or other inner surface) of the cell culture compartment or cell culture chamber. Alternatively, the agent may comprise one or more coatings covering one or more surfaces (e.g., a floor, a wall, a ceiling, or other inner surface) of the cell culture compartment or cell culture chamber. Such coatings may comprise an extracellular matrix coating such as a hydrophilic coating (e.g., collagen, fibronectin, PLL, or PDL).

The cell culture compartment or cell culture chamber may comprise one or more dimensions. For example, a cell culture compartment or cell culture chamber may have a cylindrical shape comprising a diameter and a height. Such a cylindrical cell culture compartment or cell culture chamber may have a diameter of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm. Such a cylindrical cell culture compartment or cell culture chamber may have a height of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

In some cases, a cell culture compartment or cell culture chamber may comprise a microfluidic channel having a cylindrical shape comprising a diameter and a height. Such a cylindrical cell culture compartment or cell culture chamber may have a diameter of, for example, no more than about 10 micrometers or microns ($\mu$m), no more than about 20 $\mu$m, no more than about 30 $\mu$m, no more than about 40 $\mu$m, no more than about 50 $\mu$m, no more than about 60 $\mu$m, no more than about 70 $\mu$m, no more than about 80 $\mu$m, no more than about 90 $\mu$m, no more than about 100 $\mu$m, no more than about 150 $\mu$m, no more than about 200 $\mu$m, no more than about 250 $\mu$m, no more than about 300 $\mu$m, no more than about 350 $\mu$m, no more than about 400 $\mu$m, no more than about 450 $\mu$m, no more than about 500 $\mu$m, no more than about 550 $\mu$m, no more than about 600 $\mu$m, no more than about 650 $\mu$m, no more than about 700 $\mu$m, no more than about 750 $\mu$m, no more than about 800 $\mu$m, no more than about 850 $\mu$m, no more than about 900 $\mu$m, no more than about 950 $\mu$m, or no more than about 1,000 $\mu$m. Such a cylindrical microfluidic channel may have a height of, for example, no more than about 10 micrometers or microns ($\mu$m), no more than about 20 $\mu$m, no more than about 30 $\mu$m, no more than about 40 $\mu$m, no more than about 50 $\mu$m, no more than about 60 $\mu$m, no more than about 70 $\mu$m, no more than about 80 $\mu$m, no more than about 90 $\mu$m, no more than about 100 $\mu$m, no more than about 150 $\mu$m, no more than about 200 $\mu$m, no more than about 250 $\mu$m, no more than about 300 $\mu$m, no more than about 350 $\mu$m, no more than about 400 $\mu$m, no more than about 450 $\mu$m, no more than about 500 $\mu$m, no more than about 550 $\mu$m, no more than about 600 $\mu$m, no more than about 650 $\mu$m, no more than about 700 $\mu$m, no more than about 750 $\mu$m, no more than about 800 $\mu$m, no more than about 850 $\mu$m, no more than about 900 $\mu$m, no more than about 950 $\mu$m, or no more than about 1,000 $\mu$m.

As another example, a cell culture compartment or cell culture chamber may have a rectangular shape comprising three dimensions (e.g., a length, a width, and a height). Such a rectangular cell culture compartment or cell culture chamber may have as any of its dimensions, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

In some cases, a cell culture compartment or cell culture chamber may have a rectangular shape comprising three dimensions (e.g., a length, a width, and a height). Such a rectangular cell culture compartment or cell culture chamber may have as any of its dimensions, for example, no more than about 10 micrometers or microns ($\mu$m), no more than about 20 $\mu$m, no more than about 30 $\mu$m, no more than about 40 $\mu$m, no more than about 50 $\mu$m, no more than about 60 $\mu$m, no more than about 70 $\mu$m, no more than about 80 $\mu$m, no more than about 90 $\mu$m, no more than about 100 $\mu$m, no more than about 150 $\mu$m, no more than about 200 $\mu$m, no more than about 250 $\mu$m, no more than about 300 $\mu$m, no more than about 350 $\mu$m, no more than about 400 $\mu$m, no more than about 450 $\mu$m, no more than about 500 $\mu$m, no more than about 550 $\mu$m, no more than about 600 $\mu$m, no more than about 650 $\mu$m, no more than about 700 $\mu$m, no more than about 750 $\mu$m, no more than about 800 $\mu$m, no more than about 850 $\mu$m, no more than about 900 $\mu$m, no more than about 950 $\mu$m, or no more than about 1,000 $\mu$m.

As another example, a cell culture compartment or cell culture chamber may have a spherical or hemispherical shape comprising a radius. Such a spherical or hemispherical cell culture compartment or cell culture chamber may have a radius of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 25 mm, no more than about 30 mm, no more than about 35 mm, no more than about 40 mm, no more than about 45 mm, no more than about 50 mm, no more than about 55 mm, no more than about 60 mm, no more than about 65 mm, no more than about 70 mm, no more than about 75 mm, no more than about 80 mm, no more than about 85 mm, no more than about 90 mm, no more than about 95 mm, no more than about 100 mm, no more than about 105 mm, no more than about 110 mm, no more than about 115 mm, no more than about 120 mm, no more than about 125 mm, no more than about 130 mm, no more than about 135 mm, no more than about 140 mm, no more than about 145 mm, or no more than about 150 mm.

In some cases, a cell culture compartment or cell culture chamber may have a spherical or hemispherical shape comprising a radius. Such a spherical or hemispherical cell culture compartment or cell culture chamber may have a radius of, for example, no more than about 10 micrometers or microns ($\mu$m), no more than about 20 $\mu$m, no more than about 30 $\mu$m, no more than about 40 $\mu$m, no more than about 50 $\mu$m, no more than about 60 $\mu$m, no more than about 70 $\mu$m, no more than about 80 $\mu$m, no more than about 90 $\mu$m, no more than about 100 $\mu$m, no more than about 150 $\mu$m, no more than about 200 $\mu$m, no more than about 250 $\mu$m, no more than about 300 $\mu$m, no more than about 350 $\mu$m, no more than about 400 $\mu$m, no more than about 450 $\mu$m, no more than about 500 $\mu$m, no more than about 550 $\mu$m, no more than about 600 $\mu$m, no more than about 650 $\mu$m, no more than about 700 $\mu$m, no more than about 750 $\mu$m, no more than about 800 $\mu$m, no more than about 850 $\mu$m, no more than about 900 $\mu$m, no more than about 950 $\mu$m, or no more than about 1,000 $\mu$m.

In preferred embodiments, a cell culture compartment or cell culture chamber comprises cells. For example, such cells may be animal cells, human cells, or bacterial cells. As another example, such cells may comprise a xenograft. A cell culture compartment may comprise cells obtained from an animal subject or another animal (e.g., a mouse, a rat, a hamster, a guinea pig, a rabbit, a pig, a dog, a cat, a bird, a fish, a monkey, a chimpanzee, or another type of mammal or animal). A cell culture compartment may comprise cells from a source other than the animal subject (e.g., a human subject or cell lines). A cell culture compartment may comprise cells from an animal that is younger or older than the animal subject.

In some embodiments, the cell culture device comprises one or more ports. In some embodiments, one or more ports may be connected to one or more cell culture compartments. In other embodiments, one or more ports may be connected to compartment for infusing a drug or toxin. In other embodiments, one or more ports are connected to the fluid channel. A port may be configured to function as an inlet port, e.g., to introduce a drug for performing dosing or toxicity experiments, or to infuse cell media or nutrients to the cell culture. A port may be configured to function as an output port, e.g., to exit a drug for performing dosing or toxicity experiments, or to eliminate waste products. In some embodiments, the device comprises a first and a second compartment, each compartment having one or more ports.

Any two compartments may be fluidly connected. Alternatively, any two compartments may be fluidly disconnected (e.g., distinct or separated). In some embodiments, a semi-permeable layer is positioned between the first compartment and the second compartment. Such a semi-permeable layer may be configured to selectively allow or restrict the passage of certain cell types, drugs, nutrients, waste products, or other molecules between a first compartment and a second compartment. [[flow rate and flow may be controlled via computer]]

Semi-Permeable Layer

In some embodiments, the cell culture device comprises a semi-permeable layer. In some embodiments, the semi-permeable layer is positioned between the first port and the first compartment. In some embodiments, a semi-permeable layer is positioned between one or more compartments (e.g., cell culture compartments, drug/toxin infusion compartments). In some embodiments, an epithelial cell layer serves as the semi-permeable layer separating one or more cell culture compartments or a cell culture compartment and a drug/toxin infusion compartment. In other embodiments, an epithelial cell layer is positioned between the semi-permeable layer and the first compartment.

The device may further comprise a semi-permeable layer between the channel and the compartment. The semi-permeable layer may be cell-selective. The semi-permeable layer may be size-selective.

The semi-permeable layer may allow continuous restricted fluid exchange, e.g., if the semi-permeable layer is placed between the fluid channel portion and a compartment for culturing cells. Such a semi-permeable layer may selectively restrict or allow portions of a bodily fluid to pass through the semi-permeable layer. For example, a semi-permeable layer may be configured such that all cells may be restricted from pass through the semi-permeable layer but other non-cell entities such as drugs and nutrients may be allowed (unrestricted) to pass through the semi-permeable layer. As another example, a semi-permeable layer may be configured such that all cells larger than a certain size (e.g., diameter) may be restricted from pass through the semi-permeable layer but other cells no larger than the certain size and non-cell entities such as drugs and nutrients may be allowed (unrestricted) to pass through the semi-permeable layer.

The semi-permeable layer may be a layer of cells, a lipid bilayer, a polymer gel, and/or a microporous membrane. The polymer gel may be a gel that comprises a three-dimensional cross-linked polymer network that can undergo significant deformation. The polymer gel may comprise water or some other liquid solvent that imparts deformation properties in various shapes and sizes. The polymer gel may be a soft, hydrated material that has an elastic cross-linked network with interstitial spaces that can hold a liquid solvent. The elastic cross-linked network may impart solidity as it holds a liquid solvent. The polymer gel may comprise a polymer-solvent system in which a three-dimensional network composed of polymers or their associates (aggregates) hold a large amount (tens to hundreds of times that of the polymer itself) of the solvent (e.g., water). The polymer gel can be a chemical gel. A chemical gel comprises a network of covalently crosslinked polymers that are swollen in a large amount of solvent and are generally thermally irreversible. The polymer gel can be a physical gel. A physical gel is thermally reversible and occurs as a result of intermolecular association by van der Waals forces, electrostatic forces, and/or hydrogen bonding interactions. Non-limiting examples of the polymer gel include polyvinyl alcohol (PVA), polyacrylic acid (PCA), and polyacrylonitrile (PAN).

The semi-permeable layer may comprise a biologic membrane. For example, in some cases the semi-permeable layer is comprised of a lipid bilayer.

In other cases, the semi-permeable layer is comprised of a cellular layer (e.g., epithelial cells). The layer of cells may be selected from the group consisting of epithelial cells, endothelial cells, vascular endothelial cells, pericytes, astrocytes, a multi-cell-type model of the blood-CSF barrier, choroid plexus epithelial cells, epiplexus immune cells, a multi-cell-type model of the blood-brain barrier, immune cells, or any combinations thereof. The semi-permeable layer may be a combination of pericytes and astrocytes. The semi-permeable layer may be a combination of choroid plexus epithelial cells and epiplexus immune cells.

The semi-permeable layer may comprise a microporous membrane. The microporous membrane may comprise a polymer selected from the group consisting of polyethylene terephthalate, polystyrene, cellulose acetate, cellulose nitrate, nylon, glass fiber, nylon, polyethersulfone (PES), polypropylene (PP), polytetrafluoroethylene (PTFE), hydrophilic PTFE, polyvinylidene fluoride (PVDF), hydrophilic PVDF, cellulose ester, polysulfone, etched polycarbonate, collagen, and regenerated cellulose. The collagen may be a fibrillar collagen such as collagen type I, II, III, V, and/or XI. The collagen may be a facit collagen such as collagen type IX, XII, and/or XIV. The collagen may be a short chain collagen such as collagen type VIII and/or X. The collagen may be a basement membrane collagen such as collagen type IV. The collagen may be collage type VI, VII, and/or XIII.

Such a microporous membrane may comprise a plurality of pores. Each of the plurality of pores may have the same or different pore diameters. Such pores of the semi-permeable layer may allow exchange of media, nutrients, molecules, and the passage of some or all cells (e.g., based on the pore diameter).

For example, small pore diameters of the semi-permeable layer (e.g., no more than about 0.1 micrometer or microns (μm), no more than about 0.2 μm, no more than about 0.3 μm, no more than about 0.4 μm, no more than about 0.5 μm, no more than about 0.6 μm, no more than about 0.7 μm, no more than about 0.8 μm, no more than about 0.9 μm, no more than about 1.0 μm, no more than about 1.1 μm, no more than about 1.2 μm, no more than about 1.3 μm, no more than about 1.4 μm, no more than about 1.5 μm, no more than about 1.6 μm, no more than about 1.7 μm, no more than about 1.8 μm, no more than about 1.9 μm, or no more than about 2.0 μm) may be configured to prevent cell passage of most or all cells in a bodily fluid from passing through the semi-permeable layer. Such a semi-permeable layer may be configured to allow only plasma exchange between the plenum and the cell compartment.

As another example, another size of pore diameter of the semi-permeable layer (e.g., no more than about 3.0 μm, no more than about 3.1 μm, no more than about 3.2 μm, no more than about 3.3 μm, no more than about 3.4 μm, no more than about 3.5 μm, no more than about 3.6 μm, no more than about 3.7 μm, no more than about 3.8 μm, no more than about 3.9 μm, no more than about 4.0 μm, no more than about 4.1 μm, no more than about 4.2 μm, no more than about 4.3 μm, no more than about 4.4 μm, no more than about 4.5 μm, no more than about 4.6 μm, no more than about 4.7 μm, no more than about 4.8 μm, no more than about 4.9 μm, or no more than about 5.0 μm, no more than about 5.0 μm, no more than about 5.1 μm, no more than about 5.2 μm, no more than about 5.3 μm, no more than about 5.4 μm, no more than about 5.5 μm, no more than about 5.6 μm, no more than about 5.7 μm, no more than about 5.8 μm, no more than about 5.9 μm, or no more than about 6.0 μm) may be configured to prevent cell passage of most or all cells in a bodily fluid except for platelets (e.g., each having a diameter of about 2 μm to 3 μm) from passing through the semi-permeable layer. Such a semi-permeable layer may allow certain types of cells, tissues, or small molecules (e.g., drugs) to pass through the semi-permeable barrier (e.g., from the plenum to the cell compartment, or from the cell compartment to the plenum).

As another example, another size of pore diameter of the semi-permeable layer (e.g., no more than about 8.0 μm, no more than about 8.1 μm, no more than about 8.2 μm, no more than about 8.3 μm, no more than about 8.4 μm, no more than about 8.5 μm, no more than about 8.6 μm, no more than about 8.7 μm, no more than about 8.8 μm, no more than about 8.9 μm, no more than about 9.0 μm, no more than about 9.1 μm, no more than about 9.2 μm, no more than about 9.3 μm, no more than about 9.4 μm, no more than about 9.5 μm, no more than about 9.6 μm, no more than about 9.7 μm, no more than about 9.8 μm, no more than about 9.9 μm, or no more than about 10.0 μm) may be configured to prevent cell passage of most or all cells in a bodily fluid except for platelets (e.g., each having a diameter of about 2 μm to 3 μm) and red blood cells (e.g., each having a diameter of about 6 mm to 8 mm) from passing through the semi-permeable layer.

As another example, another size of pore diameter of the semi-permeable layer (e.g., no more than about 12.0 μm, no more than about 12.1 μm, no more than about 12.2 μm, no more than about 12.3 μm, no more than about 12.4 μm, no more than about 12.5 μm, no more than about 12.6 μm, no more than about 12.7 μm, no more than about 12.8 μm, no more than about 12.9 μm, no more than about 13.0 μm, no more than about 13.1 μm, no more than about 13.2 μm, no more than about 13.3 μm, no more than about 13.4 μm, no more than about 13.5 μm, no more than about 13.6 nm, no more than about 13.7 μm, no more than about 13.8 μm, no more than about 13.9 μm, no more than about 14.0 μm, no more than about 14.1 μm, no more than about 14.2 μm, no more than about 14.3 μm, no more than about 14.4 μm, no more than about 14.5 μm, no more than about 14.6 μm, no more than about 14.7 μm, no more than about 14.8 μm, no more than about 14.9 μm, or no more than about 14.0 nm) may be configured to prevent cell passage of most or all circulating tumor cells (CTCs) in a bodily fluid but allow most normal blood cells including platelets (e.g., each having a diameter of about 2 μm to 3 μm), red blood cells (e.g., each having a diameter of about 6 μm to 8 μm), and white blood cells (e.g., most having a diameter of about 8 μm to 12 μm) to pass through the semi-permeable layer.

Other examples of sizes of pore diameters of the semi-permeable layer may be configured to prevent passage of some cell types but allow other cell types to pass through the semi-permeable layer.

The semi-permeable layer may comprise a synthetic material. Non-limiting examples of the synthetic material include cellulose acetate, cellulose nitrate, nylon, glass fiber, nylon, polyethersulfone (PES), polypropylene (PP), polytetrafluoroethylene (PTFE), hydrophilic PTFE, polyvinylidene fluoride (PVDF), hydrophilic PVDF, cellulose ester, polysulfone, etched polycarbonate, and regenerated cellulose.

The semi-permeable layer may comprise polyethylene terephthalate (PET), polystyrene, or another suitable material for a microporous membrane. The semi-permeable layer may comprise chemical properties that minimize non-specific binding of compounds and small molecules to the semi-permeable layer. The semi-permeable layer may comprise a durable material such that the semi-permeable layer will not break or deform upon normal usage and manipulation. The semi-permeable layer may comprise a membrane with transparent, translucent, and/or fluorescence-blocking optical properties. For example, a transparent semi-permeable layer may allow visualization of cells by light microscopy or other detecting methods. As another example, a translucent semi-permeable layer may exhibit high pore density suitable for certain kinds of cell studies such as compound bioavailability. As another example, a fluorescence-blocking semi-permeable layer may allow quantitative analysis of cells through fluorescence detection. The semi-permeable layer may suitable for performing a variety of different cell experiments, including angiogenesis, tumor cell biology, inflammation, toxicity, cell differentiation, drug discovery, and cell imaging studies. Experiments may be performed on a variety of cell types, such as endothelial cells, epithelial cells, red blood cells, white blood cells (leukocytes), monocytes, platelets, fibroblasts, neuronal cells, primary cells, stem cells, tumor-derived cells, etc.

The semi-permeable layer may comprise a coating. Such a coating may comprise an extracellular matrix coating, such as collagen or fibronectin. The semi-permeable layer may be sterile. The semi-permeable layer may be gamma-irradiated. The semi-permeable layer may comprise a hydrophilic surface coating and/or a hydrophilic surface modification. The semi-permeable layer may comprise a hydrophobic surface coating and/or a hydrophilic surface modification. For example, the semi-permeable layer may comprise a hydrophilic and/or neutrally charged hydrogel layer.

Cell Culture Chambers

Figure 8:
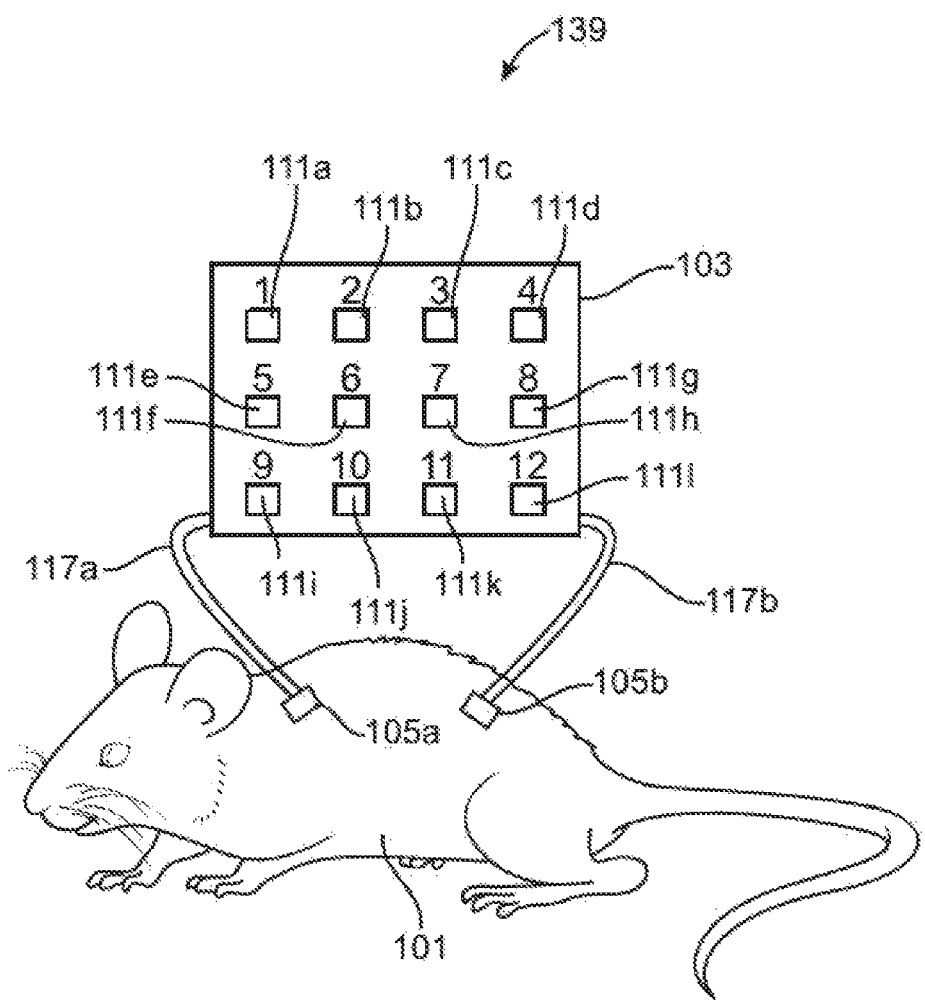
FIG. 8 illustrates an example of a multiplexed animal-chip hybrid system comprising an animal subject and a cell culture device with a plurality separate cell culture compartments.

In some embodiments, a cell culture compartment comprises a plurality of separate cell culture chambers, as illustrated in FIG. 8. For example, a cell culture compartment may comprise a plurality of N separate cell culture chambers. Such a cell culture compartment may be part of a cell culture device suitable for integrating with an animal subject into a multiplexed animal-chip hybrid system, which may be advantageous for simultaneously performing multiple cell culture operations or experiments under similar or different experimental conditions. In some cases, each chamber of the plurality of separate cell culture chambers may comprise a portion with transparent, translucent, and/or fluorescence-blocking optical properties. For example, a transparent portion (e.g., window) may allow visualization of cells within the chamber by light microscopy or other detecting methods.

For example, the plurality of N separate cell culture chambers may be placed in an array format, where each position of the array comprises a separate cell culture chamber (e.g., to perform experiments under different conditions, or to perform a different replicate of an experiment). The array may be a rectangular array. The array may be a square array. For example, each of the plurality of separate cell culture chambers may contain cells or tissues from a variety of different organs. As another example, each of the plurality of separate cell culture chambers may contain cells or tissues from a variety of different human subjects.

The plurality of N separate cell culture chambers may be configured to conduct different experiments in each of the separate cell culture chambers. For example, each separate experiment may comprise cells from a different source (e.g., a xenograft experiment from different patients). As another example, each separate experiment may comprise a different tissue type (e.g., lung, heart, etc.). As another example, each separate experiment may comprise a different small molecule (e.g., drug). As another example, each separate experiment may comprise a different dosing of a small molecule (e.g., drug). As yet another example, each separate experiment may comprise a different biologic molecule (e.g., antibody). As another example, each separate experiment may comprise a different dosing of a biologic molecule (e.g., antibody).

Integrated Device

The cell culture device may be fabricated and/or assembled as a plurality of parts (e.g., active components). Such parts may comprise, for example, a bottom layer (e.g., a layer of bulk material), a top layer, one or more cell culture compartments (or one or more toxin/drug delivery compartments) layered in between the bottom layer and the top layer, one or more valves, one or more pumps, and/or one or more columns. Such valves, pumps, and/or columns may be configured to pump fluid through the fluid channel of the device and/or pressurize the fluid channel using air or an inert gas. Multiple individually fabricated layers comprising parts may be stacked to create large arrays of parts. In other embodiments, the device is molded from a single material (e.g., an elastic material such as PDMS).

Fabrication of one or more of the parts may comprise mapping the parts using standard CAD software and transferring the mapping onto transparent photomasks. A reusable mold may be produced, e.g., using soft photolithographic techniques. A resin such as PDMS may be poured into such a reusable mold and subsequently cured by baking. The devices may be bonded to substrates (e.g., glass or silicon) for mechanical support.

The cell culture device may comprise one or more dimensions. For example, a cell culture device may have a cylindrical shape comprising a diameter and a height. Such a cylindrical cell culture device may have a diameter of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

Such a cylindrical cell culture device may have a height of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

As another example, a cell culture device may have a rectangular shape comprising three dimensions (e.g., a length, a width, and a height). Such a rectangular cell culture device may have as any of its dimensions, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 30 mm, no more than about 40 mm, no more than about 50 mm, no more than about 60 mm, no more than about 70 mm, no more than about 80 mm, no more than about 90 mm, no more than about 100 mm, no more than about 110 mm, no more than about 120 mm, no more than about 130 mm, no more than about 140 mm, no more than about 150 mm, no more than about 160 mm, no more than about 170 mm, no more than about 180 mm, no more than about 190 mm, no more than about 200 mm, no more than about 210 mm, no more than about 220 mm, no more than about 230 mm, no more than about 240 mm, no more than about 250 mm, no more than about 260 mm, no more than about 270 mm, no more than about 280 mm, no more than about 290 mm, or no more than about 300 mm.

As another example, a cell culture device may have a spherical or hemispherical shape comprising a radius. Such a spherical or hemispherical cell culture device may have a radius of, for example, no more than about 1 millimeter (mm), no more than about 2 mm, no more than about 3 mm, no more than about 4 mm, no more than about 5 mm, no more than about 6 mm, no more than about 7 mm, no more than about 8 mm, no more than about 9 mm, no more than about 10 mm, no more than about 15 mm, no more than about 20 mm, no more than about 25 mm, no more than about 30 mm, no more than about 35 mm, no more than about 40 mm, no more than about 45 mm, no more than about 50 mm, no more than about 55 mm, no more than about 60 mm, no more than about 65 mm, no more than about 70 mm, no more than about 75 mm, no more than about 80 mm, no more than about 85 mm, no more than about 90 mm, no more than about 95 mm, no more than about 100 mm, no more than about 105 mm, no more than about 110 mm, no more than about 115 mm, no more than about 120 mm, no more than about 125 mm, no more than about 130 mm, no more than about 135 mm, no more than about 140 mm, no more than about 145 mm, or no more than about 150 mm.

The cell culture device may be configured to hold an overall volume of fluid. Such an overall volume may vary depending on the geometry, shape, and/or dimensions of the cell culture compartments or cell culture chambers and of the fluid channel of the device. Such an overall volume of the device may be no more than about 1 microliter (µL), no more than about 2 µL, no more than about 3 µL, no more than about 4 µL, no more than about 5 µL, no more than about 6 µL, no more than about 7 µL, no more than about 8 µL, no more than about 9 µL, no more than about 10 µL, no more than about 20 µL, no more than about 30 µL, no more than about 40 µL, no more than about 50 µL no more than about 60 µL, no more than about 70 µL, no more than about 80 µL no more than about 90 µL, no more than about 100 µL, no more than about 200 µL, no more than about 300 µL, no more than about 400 µL, no more than about 500 µL, no more than about 600 µL, no more than about 700 µL, no more than about 800 µL, no more than about 900 µL, no more than about 1 mL, no more than about 2 mL, no more than about 3 mL, no more than about 4 mL, no more than about 5 mL, no more than about 6 mL, no more than about 7 mL, no more than about 8 mL, no more than about 9 mL, no more than about 10 mL, no more than about 20 mL, no more than about 30 mL, no more than about 40 mL, no more than about 50 mL, no more than about 60 mL, no more than about 70 mL, no more than about 80 mL, no more than about 90 mL, no more than about 100 mL, no more than about 200 mL, no more than about 300 mL, no more than about 400 mL, no more than about 500 mL, no more than about 600 mL, no more than about 700 mL, no more than about 800 mL, no more than about 900 mL, no more than about 1 L, no more than about 2 L, no more than about 3 L, no more than about 4 L, no more than about 5 L, no more than about 6 L, no more than about 7 L, no more than about 8 L, no more than about 9 L, or no more than about 10 L.

The cell culture device may be configured to allow a flow-through rate (or flow rate) of fluid through the fluid channel of the device. Such a flow rate of the device may vary depending on the geometry, shape, and/or dimensions of the cell culture compartments or cell culture chambers and of the fluid channel of the device, and/or on the pumping mechanism used to pressurize the fluid flow. Such an flow rate of the device may be no more than about 1 microliter (µL) per minute (min), no more than about 2 µL per min (µL/min), no more than about 3 µL/min, no more than about 4 µL/min, no more than about 5 µL/min, no more than about 6 µL/min, no more than about 7 µL/min, no more than about 8 µL/min, no more than about 9 µL/min, no more than about 10 µL/min, no more than about 20 µL/min, no more than about 30 µL/min, no more than about 40 µL/min, no more than about 50 µL/min, no more than about 60 µL/min, no more than about 70 µL/min, no more than about 80 µL/min, no more than about 90 µL/min, no more than about 100 µL/min, no more than about 200 µL/min, no more than about 300 µL/min, no more than about 400 µL/min, no more than about 500 µL/min, no more than about 600 µL/min, no more than about 700 µL/min, no more than about 800 µL/min, no more than about 900 µL/min, no more than about 1 mL/min, no more than about 2 mL/min, no more than about 3 mL/min, no more than about 4 mL/min, no more than about 5 mL/min, no more than about 6 mL/min, no more than about 7 mL/min, no more than about 8 mL/min, no more than about 9 mL/min, no more than about 10 mL/min, no more than about 20 mL/min, no more than about 30 mL/min, no more than about 40 mL/min, no more than about 50 mL/min, no more than about 60 mL/min, no more than about 70 mL/min, no more than about 80 mL/min, no more than about 90 mL/min, no more than about 100 mL/min, no more than about 200 mL/min, no more than about 300 mL/min, no more than about 400 mL/min, no more than about 500 mL/min, no more than about 600 mL/min, no more than about 700 mL/min, no more than about 800 mL/min, no more than about 900 mL/min, no more than about 1 L/min, no more than about 2 L/min, no more than about 3 L/min, no more than about 4 L/min, no more than about 5 L/min, no more than about 6 L/min, no more than about 7 L/min, no more than about 8 L/min, no more than about 9 L/min, or no more than about 10 L/min.

Infusion System

The infusion system may comprise one or more of: a controller, a holder, a pump, valves, manifolds, tubing, drip chambers, flow regulators, and syringes. The infusion system may comprise the cell culture device 103 and one or more of: a controller, a holder, a pump, valves, manifolds, tubing, drip chambers, flow regulators, and syringes. The infusion system may comprise a controller configured to manually or automatically control valve switching, pumping mechanisms (e.g., with a variable or constant fluid flow rate), and other actions of the infusion system. The infusion system may comprise a holder (e.g., a magnetic holder) suitable for mounting some portions of or all of the infusion system (e.g., to a base). The infusion system may comprise a pump (e.g., a peristaltic pump), valves, manifolds, and/or tubing suitable for connecting to the cell culture device and selectable (e.g., manually or automatically) controlling a pumping mechanism (e.g., with a variable or constant fluid flow rate) of the infusion system applied on the fluid flowing through the device during perfusion. The pump, valves, manifolds, and/or tubing may be sized appropriately to allow or restrict the fluid flow rate to within one or more desired levels or ranges. The pump, valves, manifolds, and/or tubing may be sized appropriately to allow continuous or intermittent perfusion of a fluid through the cell culture compartments of the cell culture device with a given size. The infusion system may comprise a drip chamber suitable to allow gas to precipitate out of the fluid being flowed through the fluid channel of the device. The infusion system may comprise a syringe suitable for injecting one or more substances (e.g., a drug, a toxin, a nutrient, or other experimental reagent) into the cell culture compartments and/or fluid channel of the device for perfusion.

The infusion system may be configured to apply a flow-through rate (or flow rate) of fluid (e.g., through the fluid channel of the device and/or through any tubing that is part of the infusion system). Such a flow rate of the infusion system (e.g., through the device) may vary depending on the geometry, shape, and/or dimensions of the cell culture compartments or cell culture chambers and of the fluid channel of the device, and/or on the pumping mechanism of the infusion system used to pressurize the fluid flow. Such an flow rate of the infusion system may be no more than about 1 microliter (µL) per minute (min), no more than about 2 µL per min (µL/min), no more than about 3 µL/min, no more than about 4 µL/min, no more than about 5 µL/min, no more than about 6 µL/min, no more than about 7 µL/min, no more than about 8 µL/min, no more than about 9 µL/min, no more than about 10 µL/min, no more than about 20 µL/min, no more than about 30 µL/min, no more than about 40 pt/min, no more than about 50 µL/min, no more than about 60 µL/min, no more than about 70 µL/min, no more than about 80 µL/min, no more than about 90 µL/min, no more than about 100 µL/min, no more than about 200 µL/min, no more than about 300 µL/min, no more than about 400 µL/min, no more than about 500 µL/min, no more than about 600 µL/min, no more than about 700 µL/min, no more than about 800 µL/min, no more than about 900 µL/min, no more than about 1 mL/min, no more than about 2 mL/min, no more than about 3 mL/min, no more than about 4 mL/min, no more than about 5 mL/min, no more than about 6 mL/min, no more than about 7 mL/min, no more than about 8 mL/min, no more than about 9 mL/min, no more than about 10 mL/min, no more than about 20 mL/min, no more than about 30 mL/min, no more than about 40 mL/min, no more than about 50 mL/min, no more than about 60 mL/min, no more than about 70 mL/min, no more than about 80 mL/min, no more than about 90 mL/min, no more than about 100 mL/min, no more than about 200 mL/min, no more than about 300 mL/min, no more than about 400 mL/min, no more than about 500 mL/min, no more than about 600 mL/min, no more than about 700 mL/min, no more than about 800 mL/min, no more than about 900 mL/min, no more than about 1 L/min, no more than about 2 L/min, no more than about 3 L/min, no more than about 4 L/min, no more than about 5 L/min, no more than about 6 L/min, no more than about 7 L/min, no more than about 8 L/min, no more than about 9 L/min, or no more than about 10 L/min.

The infusion system may be mechanically attached to the animal subject through any suitable attachment mechanism. Such an attachment mechanism may comprise one or more of: glues, adhesives, backing materials coated with an adhesive, tubing, sutures, swivels, tethers, clips, hooks, clamps, a collar, a helmet, a vest, a harness, a jacket, and a patch. For example, the infusion system may be attached around the neck of the animal subject using a collar. As another example, the infusion system may be attached to the head of the animal subject using a helmet. As another example, the infusion system may be attached to the body of the animal subject using a jacket, a vest, or a patch. The attachment mechanism may enable the infusion system to perform perfusion (e.g., continuous or intermittent) of the animal subject while being mechanically attached to the animal subject. The attachment mechanism may enable the infusion system to be semi-permanently attached to the animal subject (e.g., for periods of at least about 24 hours). Alternatively, the attachment mechanism may enable the infusion system to be temporarily attached to the animal subject for a time sufficient to perform experiments (e.g., for no more than about 5 minutes, no more than about 10 minutes, no more than about 15 minutes, no more than about 20 minutes, no more than about 30 minutes, no more than about 40 minutes, no more than about 50 minutes, no more than about 60 minutes, no more than about 2 hours, no more than about 3 hours, no more than about 4 hours, no more than about 6 hours, no more than about 8 hours, no more than about 10 hours, no more than about 12 hours, no more than about 14 hours, no more than about 16 hours, no more than about 18 hours, no more than about 20 hours, no more than about 22 hours, or no more than about 24 hours).

In some embodiments, the cell culture device is attached to the animal for at least 24 hours, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 45 days, at least 60 days, at least 75 days, at least 90 days, at least 120 days, at least 150 days, or at least 180 days.

Detector

In some embodiments, a system comprises the cell culture device and a detector, wherein a cell culture compartment comprises cells, and wherein the detector measures one or more parameters associated with the cell culture compartment or the cells. In some embodiments, the detector is operatively coupled to the cell culture device. The detector may be any apparatus suitable for detecting and measuring one or more parameters associated with the cell culture compartment or the cells. The detector may be configured to measure one or more of a variety of parameters, such as solution flow, temperature, morphology, color, fluorescence, luminescence, pH, or electrochemical properties.

For example, the detector may comprise a fluid flow meter configured to measure solution flow (e.g., flow of a bodily fluid such as blood through the cell culture compartment of the device). As another example, the detector may comprise a thermometer or other similar device configured to measure temperature (e.g., of a bodily fluid such as blood in the cell culture compartment of the device). As another example, the detector may comprise a microscope or other similar optical instrument configured to measure morphology (e.g., cell morphology of the cells in the cell culture compartment of the device). As another example, the detector may comprise a camera (e.g., a charge-coupled device (CCD) camera or other digital camera) configured to measure images (e.g., images of the cells in the cell culture compartment of the cell culture device). As another example, the detector may comprise a fluorescence detector (or fluorescence microscope) configured to measure fluorescence (e.g., fluorescence of the cells in the cell culture compartment of the device). As another example, the detector may comprise a luminescence sensor (or other similar photometer) configured to measure luminescence (e.g., luminescence of the cells in the cell culture compartment of the device). As another example, the detector may comprise a pH meter configured to measure pH (e.g., pH of the cells in the cell culture compartment of the device). As another example, the detector may comprise an electrochemical detector configured to measure electrochemical properties (e.g., electrochemical properties of the cells in the cell culture compartment of the device). As another example, the detector may comprise a radio-frequency identification (RFID) transponder configured to measure an identity (e.g., of the animal subject). In some embodiments, the detector is operatively coupled to a camera that is unattached to the animal subject. In some embodiments, the status of the detector is read by the camera that is unattached to the animal subject. In some embodiments, the detector is operatively coupled to the computer system. In some embodiments, the status of the detector is ready by a computer system.

Methods

Another aspect of the present disclosure provides a method for processing or analyzing biological material. The method may comprise providing a device comprising (1) a housing comprising (i) a channel having an inlet and an outlet, wherein the inlet and the outlet of the channel are configured to bring the channel in fluid communication with a circulatory system of a subject when the housing is secured to the subject, and (ii) a compartment fluidly connected to the channel, which compartment is configured to process or analyze the biological material; and (2) a fastener configured to secure the housing to a body of the subject. Next, the method may comprise using the fastener to secure the housing to the body of the subject.

The method may further comprise bringing the inlet and the outlet in fluid communication with the circulatory system of the subject. For example, the inlet and/or outlet may be connected to a port that is further connected to a blood vessel port in the subject. The biological material may be subjected to fluid from the circulatory system of the subject. The biological material may be subjected to the fluid in a continuous manner biological material may be subjected to the fluid in an intermittent manner.

The biological material may be a cell or a xenograft. The cell may be a human cell, an animal cell, or a bacterial cell. The cell may be selected from the group consisting of endothelial cells, epithelial cells, red blood cells, white blood cells (leukocytes), monocytes, platelets, fibroblasts, neuronal cells, primary cells, stem cells, or tumor-derived cells.

In another aspect, disclosed herein is a method for cell culture. The method for cell culture may comprise depositing cells into a cell culture compartment or cell culture chamber of a cell culture device. Next, the method for cell culture may comprise perfusing blood from an animal subject into the cell culture device. For example, the blood may enter the device at the first port and exit the device at the second port. Such perfusing may be continuous or intermittent, as described elsewhere herein. In one embodiment, the perfusion is intermittent. In some cases, such intermittent perfusion allows for the cell culture device to be detached from the animal subject for further manipulation and/or analysis. Following such detachment, in some cases the cell culture device may be reattached to the animal subject to continue continuous or intermittent perfusion as described herein. In a preferred embodiment, the perfusion is continuous while the cell culture device is attached to the animal subject.

FIG. 1 illustrates an example of an animal-chip hybrid system 100 comprising an animal subject 101 and a cell culture device 103, in accordance with some embodiments. The animal subject may be a human subject or a laboratory animal subject. In some cases, a drug or a toxin may be dosed to the animal subject via administration to the infusion system as shown.

The hybrid in vitro-in vivo cell culture system 100 may comprise a first channel 117a and a second channel 117b, as illustrated in FIG. 1. The first channel 117a may have a first end 143a and a second end 143b. The first end 143a of the first channel 117a may connect to a first blood vessel port 105a and the second end 143b of the first channel 117a may connect to a first port (not shown in FIGS. 1-7) in the cell culture device 103. The first port that connects to the second end 143b of the first channel 117a may be an inlet port. The inlet port may be an injection port. The inlet port may fluidly connect the first channel 117a with the fluid channel (not shown in FIG. 1) of the cell culture device 103, thereby allowing a fluid in the first channel 117a to enter the cell culture device 103 (e.g., into the fluid channel of the device). The first blood vessel port 105a may allow a fluid to exit the animal subject 101 (e.g., blood may exit out of a blood vessel of the animal subject 101) and enter the first channel 117a.

The second channel 117b may have a first end 145a and a second end 145b. The first end 145a of the second channel 117b may be in contact with a second port (not shown in FIGS. 1-7) that is in fluid connection with the cell culture device 103. The second port that connects to the first end 145a of the second channel 117b may be an outlet port. The outlet port may be an injection port. The second port may be in fluid connection with the fluid channel (not shown in FIG. 1) of the cell culture device 103. The second port in the cell culture device 103 may allow a fluid in the cell culture device 103 to exit the cell culture device 103 (e.g., out of the fluid channel of the device) and enter the second channel 117b. The second channel 117b may connect to a second blood vessel port 105b, as shown in FIG. 1. The second blood vessel port 105b may connect to the second end 143b of the second channel 117b and may allow a fluid to enter the animal subject 101 (e.g., fluid may enter a blood vessel of the animal subject 101). The fluid may be a bodily fluid (e.g., blood or plasma). The blood vessel ports may be in fluid connection with a blood vessel of the animal subject. For example, the blood vessel ports may connect to a vein of the animal subject.

Non-limiting examples of veins that can be connected to the blood vessel ports include a right external jugular vein, a left internal jugular vein, a right axillary vein, a left cranial vena cava, a right subclavian vein, a caudal vena cava, a hepatic vein, a left renal vein, a hepatic portal vein, a splenic vein, a mesenteric vein, a gastric vein, a right genital vein, a left iliolumbar vein, a right iliac vein a right femoral vein, a caudal vein, and a tail vein. In another example, the blood vessel ports may connect to an artery of the animal subject. Non-limiting examples of arteries that can be connected to the blood vessel ports include a right external carotid artery, a left carotid artery, a right common carotid artery, a right subclavian artery, a right axillary artery, a left axillary artery, an aortic arch, a brachiocephalic artery, a left subclavian artery, a left mammary artery, a right mammary artery, a hepatic artery, a celiac artery, a gastric artery, a splenic artery, a superior mesenteric artery, left renal artery, a right renal artery, a left genital artery, a right iliolumbar artery, a left iliac artery, a caudal artery, a tail artery, a left femoral artery, and a right femoral artery.

Alternatively, the fluid entering the animal subject and/or the fluid channel of the cell culture device may be a cell medium fluid suitable for performing cell culture. In another example, the fluid entering the animal subject and/or the fluid channel of the cell culture device may be a combination of a bodily fluid and a cell medium fluid. Non-limiting examples of a cell medium fluid include Dulbecco's Modified Eagle Medium (DMEM), Eagle's Minimum Essential Media (EMEM), Roswell Park Memorial Institute (RPMI) 1640 medium, Iscove's Modified Dulbecco's Medium (IMDM), DMEM/F12 medium, Leibovitz's L-15 medium, a reduced-serum medium, a basal medium, and a serum-free medium.

The first channel 117a and the second channel 117b may reversibly connect with any one of the ports described herein via a luer lock connector, a compression fitting, an adapter, a coupling, a quick connect hose fitting, a syringe, or any other suitable fitting. Alternatively, the first fluid channel 117a and the second fluid channel 117b may be non-reversibly connected to the cell culture device 103.

The subject may be a mammal. The mammal may be an animal or a human. The animal may be selected from the group consisting of a mouse, a rat, a hamster, a guinea pig, a rabbit, a pig, a dog, a cat, a bird, a fish, a monkey. The monkey may be a chimpanzee. The animal subject may be a human subject. A human-chip hybrid system may be advantageous, for example, as a safer form of "pre-phase I" trials. Such "pre-phase I" trials may comprise a trial run on a particular compound for a particular human subject (e.g., to administer a compound to potentially treat a condition of the particular human subject). For example, the cell culture device may be attached to an animal subject and the cell culture device may comprise cells from a human subject. Alternatively, the cell culture device may be attached to a human subject and the cell culture device may comprise cells from a human subject. In some cases, the cell culture device may be attached to the same human subject whose cells are cultured in the cell culture device as described herein. In other cases, the cell culture device may be attached to a different human subject whose cells are cultured in the cell culture device as described herein. In an example, the human-chip hybrid system may comprise a cell culture device that may be implanted subcutaneously in the human subject. In such a case, the cell culture device may have one or more ports open and in contact with bodily fluids and/or tissues of the human subject. In other cases, the cell culture device may have one or more ports closed in order to avoid contact with bodily fluids and/or tissues of the human subject. The cell culture device may be a cell culture chip.

The animal-chip hybrid system may allow "parabiosis" between the animal subject and the chip, such that a hybrid in vitro/in vivo environment is set up to allow cell culture in more natural conditions compared to an in vitro environment. Such an animal-chip hybrid system may be advantageous and enable a variety of experiments or other operations to be performed. For example, an animal-chip hybrid system may allow dosing experiments wherein a series of predetermined doses (e.g., constant, increasing, or decreasing over time) are administered to the animal subject or to the cells cultured in the cell culture device (e.g., continuously or at a series of predetermined time points).

As another example, heterochronic experiments may be performed, for example by culturing cells from an older mouse in a chip coupled to a young mouse as the animal subject. As another example, allogeneic experiments may be performed even without using immunocompromised animal subjects, since immune cells from the circulation of the animal subject may be blocked (e.g., using a semi-permeable layer or an epithelial layer) from entering a cell culture chamber and interacting with the culturing cells. For example, xenograft experiments may be performed, for example by culturing patient xenografts (e.g., cells or tissue from each of one or more human patients) in a chip coupled to an animal subject (e.g., a mouse) using such an animal-chip hybrid system.

FIG. 2 illustrates an example of an integrated animal-chip hybrid system 100 comprising an animal subject 101 and an elastic cell culture device 104 that is mechanically attached to the animal subject 101, in accordance with some embodiments described herein. The elastic cell culture device 104 is configured to be mechanically attached to the animal subject 101, for a number of advantageous purposes, e.g., to allow more natural movements of the animal subject (e.g., continual movement including locomotion and respiration to minimize metabolic or other stresses on the animal subject), to avoid a distortion of body shape of the animal subject, to induce a distortion of the chip via the mechanical attachment (e.g., for experimental purposes), etc.

The elastic cell culture device 104 may be mechanically attached to the animal subject via a first mechanical attachment 141a and a second mechanical attachment 141b, as shown in FIG. 2. The first mechanical attachment 141a and the second mechanical attachment 141b may connect to a first blood vessel port 105 and a second blood vessel port 105b, respectively. A variety of attachments may be used to mechanically attach the elastic cell culture device 104 to the animal subject 101. The first mechanical attachment 141a and the second mechanical attachment 141b may be an adhesive, a backing material coated with an adhesive, tubing, a suture, a swivel, a tether, a clip, a harness, a mesh, a helmet, a jacket, a patch, or a band.

Alternatively, the first mechanical attachment 141a and the second mechanical attachment 141b may connect directly to a vein and/or an artery. Such a configuration may allow, for example, blood perfusion (e.g., continuous or intermittent) from the animal subject 101 to the fluid channel (not shown in FIG. 2) of the elastic cell culture device 104. Such blood perfusion may be performed by configuring blood to enter the fluid channel of the elastic cell culture device 104 through a first port and to exit the fluid channel of the elastic cell culture device 104 through a second port, thereby providing perfusion to one of more cell culture compartments and/or one or more cell culture chambers.

The elastic cell culture device 104 may comprise a first channel 117a and a second channel 117b. The first channel 117a may connect to the first blood vessel port 105a on one end and connect to the elastic cell culture device 104 on the other end. The first channel 117a may facilitate fluid flow from the first blood vessel port 105a into the elastic cell culture device 104, as shown by the arrows in FIG. 2. Similarly, the second channel 117b may connect to the second blood vessel port 105b on one end and connect to the elastic cell culture device 104 on the other end. The second channel 117b may facilitate fluid flow from the elastic cell culture device 104 into the second blood vessel port 105b, as shown by the arrows in FIG. 2. The first channel 117a and the second channel 117b may be tubing, a catheter, catheter tubing, a syringe, or a combination thereof. The first blood vessel port 105a and the second blood vessel port 105b may be injection ports. The first blood vessel port 105a and the second blood vessel port 105b may comprise a catheter and/or catheter tubing.

Non-limiting examples of catheters include thoracic jugular catheters, thoracic carotid artery catheters, tail vein catheters, femoral vein catheters, femoral artery catheters, intrathecal catheters, intracranial catheters, double lumen catheters, stereotaxic brain lesioning catheters, bladder catheters, bile duct and/or duodenal catheters, and molecular imaging catheters. Non-limiting examples of tubing include silicone rubber tubing, high fidelity pressure tubing, polyethylene tubing, Tygon® tubing, polyurethane tubing, polytetrafluoroethylene (PTFE) tubing, and PTFE Heat Shrink® tubing. Non-limiting examples of catheter tubing include silicone rubber tubing, high fidelity pressure tubing, polyethylene tubing, Tygon® tubing, polyurethane tubing, polytetrafluoroethylene (PTFE) tubing, and PTFE Heat Shrink® tubing.

The tubing may have an outer diameter of about 0.005 inches to about 0.2 inches. The tubing may have an outer diameter of at least about 0.005 inches. The tubing may have an outer diameter of at most about 0.2 inches. The tubing may have an outer diameter of about 0.005 inches to about 0.01 inches, about 0.005 inches to about 0.02 inches, about 0.005 inches to about 0.03 inches, about 0.005 inches to about 0.04 inches, about 0.005 inches to about 0.05 inches, about 0.005 inches to about 0.06 inches, about 0.005 inches to about 0.07 inches, about 0.005 inches to about 0.08 inches, about 0.005 inches to about 0.09 inches, about 0.005 inches to about 0.1 inches, about 0.005 inches to about 0.2 inches, about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.01 inches to about 0.07 inches, about 0.01 inches to about 0.08 inches, about 0.01 inches to about 0.09 inches, about 0.01 inches to about 0.1 inches, about 0.01 inches to about 0.2 inches, about 0.02 inches to about 0.03 inches, about 0.02 inches to about 0.04 inches, about 0.02 inches to about 0.05 inches, about 0.02 inches to about 0.06 inches, about 0.02 inches to about 0.07 inches, about 0.02 inches to about 0.08 inches, about 0.02 inches to about 0.09 inches, about 0.02 inches to about 0.1 inches, about 0.02 inches to about 0.2 inches, about 0.03 inches to about 0.04 inches, about 0.03 inches to about 0.05 inches, about 0.03 inches to about 0.06 inches, about 0.03 inches to about 0.07 inches, about 0.03 inches to about 0.08 inches, about 0.03 inches to about 0.09 inches, about 0.03 inches to about 0.1 inches, about 0.03 inches to about 0.2 inches, about 0.04 inches to about 0.05 inches, about 0.04 inches to about 0.06 inches, about 0.04 inches to about 0.07 inches, about 0.04 inches to about 0.08 inches, about 0.04 inches to about 0.09 inches, about 0.04 inches to about 0.1 inches, about 0.04 inches to about 0.2 inches, about 0.05 inches to about 0.06 inches, about 0.05 inches to about 0.07 inches, about 0.05 inches to about 0.08 inches, about 0.05 inches to about 0.09 inches, about 0.05 inches to about 0.1 inches, about 0.05 inches to about 0.2 inches, about 0.06 inches to about 0.07 inches, about 0.06 inches to about 0.08 inches, about 0.06 inches to about 0.09 inches, about 0.06 inches to about 0.1 inches, about 0.06 inches to about 0.2 inches, about 0.07 inches to about 0.08 inches, about 0.07 inches to about 0.09 inches, about 0.07 inches to about 0.1 inches, about 0.07 inches to about 0.2 inches, about 0.08 inches to about 0.09 inches, about 0.08 inches to about 0.1 inches, about 0.08 inches to about 0.2 inches, about 0.09 inches to about 0.1 inches, about 0.09 inches to about 0.2 inches, or about 0.1 inches to about 0.2 inches. The tubing may have an outer diameter of about 0.005 inches, about 0.01 inches, about 0.02 inches, about 0.03 inches, about 0.04 inches, about 0.05 inches, about 0.06 inches, about 0.07 inches, about 0.08 inches, about 0.09 inches, about 0.1 inches, or about 0.2 inches.

The tubing may have an inner diameter of about 0.005 inches to about 0.2 inches. The tubing may have an inner diameter of at least about 0.005 inches. The tubing may have an inner diameter of at most about 0.2 inches. The tubing may have an inner diameter of about 0.005 inches to about 0.01 inches, about 0.005 inches to about 0.02 inches, about 0.005 inches to about 0.03 inches, about 0.005 inches to about 0.04 inches, about 0.005 inches to about 0.05 inches, about 0.005 inches to about 0.06 inches, about 0.005 inches to about 0.07 inches, about 0.005 inches to about 0.08 inches, about 0.005 inches to about 0.09 inches, about 0.005 inches to about 0.1 inches, about 0.005 inches to about 0.2 inches, about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.01 inches to about 0.07 inches, about 0.01 inches to about 0.08 inches, about 0.01 inches to about 0.09 inches, about 0.01 inches to about 0.1 inches, about 0.01 inches to about 0.2 inches, about 0.02 inches to about 0.03 inches, about 0.02 inches to about 0.04 inches, about 0.02 inches to about 0.05 inches, about 0.02 inches to about 0.06 inches, about 0.02 inches to about 0.07 inches, about 0.02 inches to about 0.08 inches, about 0.02 inches to about 0.09 inches, about 0.02 inches to about 0.1 inches, about 0.02 inches to about 0.2 inches, about 0.03 inches to about 0.04 inches, about 0.03 inches to about 0.05 inches, about 0.03 inches to about 0.06 inches, about 0.03 inches to about 0.07 inches, about 0.03 inches to about 0.08 inches, about 0.03 inches to about 0.09 inches, about 0.03 inches to about 0.1 inches, about 0.03 inches to about 0.2 inches, about 0.04 inches to about 0.05 inches, about 0.04 inches to about 0.06 inches, about 0.04 inches to about 0.07 inches, about 0.04 inches to about 0.08 inches, about 0.04 inches to about 0.09 inches, about 0.04 inches to about 0.1 inches, about 0.04 inches to about 0.2 inches, about 0.05 inches to about 0.06 inches, about 0.05 inches to about 0.07 inches, about 0.05 inches to about 0.08 inches, about 0.05 inches to about 0.09 inches, about 0.05 inches to about 0.1 inches, about 0.05 inches to about 0.2 inches, about 0.06 inches to about 0.07 inches, about 0.06 inches to about 0.08 inches, about 0.06 inches to about 0.09 inches, about 0.06 inches to about 0.1 inches, about 0.06 inches to about 0.2 inches, about 0.07 inches to about 0.08 inches, about 0.07 inches to about 0.09 inches, about 0.07 inches to about 0.1 inches, about 0.07 inches to about 0.2 inches, about 0.08 inches to about 0.09 inches, about 0.08 inches to about 0.1 inches, about 0.08 inches to about 0.2 inches, about 0.09 inches to about 0.1 inches, about 0.09 inches to about 0.2 inches, or about 0.1 inches to about 0.2 inches. The tubing may have an inner diameter of about 0.005 inches, about 0.01 inches, about 0.02 inches, about 0.03 inches, about 0.04 inches, about 0.05 inches, about 0.06 inches, about 0.07 inches, about 0.08 inches, about 0.09 inches, about 0.1 inches, or about 0.2 inches.

Alternatively, the elastic cell culture device may not comprise a first channel 117a and/or a second channel 117b. For example, in this case, the cell culture device may be implanted subcutaneously in the animal subject. In this case, the first port and second port (not shown in FIG. 2) of the elastic cell culture device may be left open in order to cause the fluid channel of the elastic cell culture device to be in contact with any bodily fluid and/or subcutaneous tissue of the animal subject. Any one of the ports of the elastic cell culture device may be open and/or closed when subcutaneously implanting the elastic cell culture device.

The elastic cell culture device 104 may be comprised of any elastic material, such as polydimethylsiloxane (PDMS).

The elastic cell culture device 104 may comprise an elastic material and a glass material. The elastic material may have an elastic modulus ranging from about 130 to about 180 gigapascals (GPa). The elastic material may have an elastic modulus ranging from about 100 GPa to about 200 GPa. The elastic material may have an elastic modulus ranging from at least about 100 GPa. The elastic material may have an elastic modulus ranging from at most about 200 GPa. The elastic material may have an elastic modulus ranging from about 100 GPa to about 110 GPa, about 100 GPa to about 120 GPa, about 100 GPa to about 130 GPa, about 100 GPa to about 140 GPa, about 100 GPa to about 150 GPa, about 100 GPa to about 160 GPa, about 100 GPa to about 170 GPa, about 100 GPa to about 180 GPa, about 100 GPa to about 190 GPa, about 100 GPa to about 200 GPa, about 110 GPa to about 120 GPa, about 110 GPa to about 130 GPa, about 110 GPa to about 140 GPa, about 110 GPa to about 150 GPa, about 110 GPa to about 160 GPa, about 110 GPa to about 170 GPa, about 110 GPa to about 180 GPa, about 110 GPa to about 190 GPa, about 110 GPa to about 200 GPa, about 120 GPa to about 130 GPa, about 120 GPa to about 140 GPa, about 120 GPa to about 150 GPa, about 120 GPa to about 160 GPa, about 120 GPa to about 170 GPa, about 120 GPa to about 180 GPa, about 120 GPa to about 190 GPa, about 120 GPa to about 200 GPa, about 130 GPa to about 140 GPa, about 130 GPa to about 150 GPa, about 130 GPa to about 160 GPa, about 130 GPa to about 170 GPa, about 130 GPa to about 180 GPa, about 130 GPa to about 190 GPa, about 130 GPa to about 200 GPa, about 140 GPa to about 150 GPa, about 140 GPa to about 160 GPa, about 140 GPa to about 170 GPa, about 140 GPa to about 180 GPa, about 140 GPa to about 190 GPa, about 140 GPa to about 200 GPa, about 150 GPa to about 160 GPa, about 150 GPa to about 170 GPa, about 150 GPa to about 180 GPa, about 150 GPa to about 190 GPa, about 150 GPa to about 200 GPa, about 160 GPa to about 170 GPa, about 160 GPa to about 180 GPa, about 160 GPa to about 190 GPa, about 160 GPa to about 200 GPa, about 170 GPa to about 180 GPa, about 170 GPa to about 190 GPa, about 170 GPa to about 200 GPa, about 180 GPa to about 190 GPa, about 180 GPa to about 200 GPa, or about 190 GPa to about 200 GPa. The elastic material may have an elastic modulus ranging from about 100 GPa, about 110 GPa, about 120 GPa, about 130 GPa, about 140 GPa, about 150 GPa, about 160 GPa, about 170 GPa, about 180 GPa, about 190 GPa, or about 200 GPa.

The elastic cell culture device 104 may comprise an inorganic material, a polymeric material, a metal, a paper material, or any combination thereof. Non-limiting examples of the inorganic material that the elastic cell culture device 104 may comprise include a silicon material, a ceramic material, and a glass material. Non-limiting examples of the polymeric material that the elastic cell culture device 104 may comprise include an elastomeric material (e.g., PDMS), a thermoset polyester, a thermoplastic polymer, polystyrene, polycarbonate, poly-methyl methacrylate (PMMA), poly-ethylene glycol diacrylate (PEGDA), perfluorinated compounds (e.g., perfluoroalkoxy alkane, fluorinated ethylene propylene, photocurable perfluoropolyether, and polyfluoropolyether diol methacrylate), poly(N-isopropylacrylamide) (PNIPAAm), and polyurethane (PU). Non-limiting examples of the polymeric material that the elastic cell culture device 104 may comprise include gold and iron (e.g., in the form of nanoparticles, nanofibers, nanowires, and/or nanopillars). The elastic cell culture device 104 may comprise a hydrogel. Non-limiting examples of materials that the hydrogel may be comprised of include an extracellular matrix material (e.g., collagen, fibrin, and/or laminin), alginate, hyaluronic acid, agarose, and gelatin.

Figure 3:
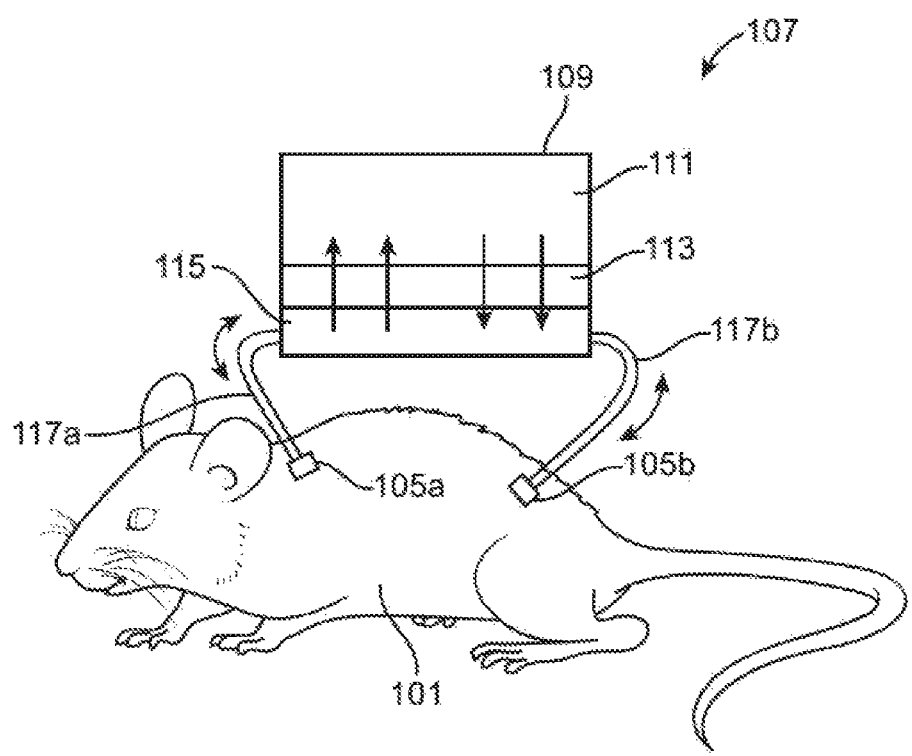
FIG. 3 illustrates an example of a "plasma-exchange" animal-chip hybrid system comprising an animal subject and a cell culture device with a semi-permeable barrier positioned between the plenum and a cell culture compartment, in accordance with some embodiments.

FIG. 3 illustrates an example of a "plasma-exchange" animal-chip hybrid system 107 comprising an animal subject 101 and a plasma exchange cell culture device 109. The plasma-exchange animal-hip hybrid system 107 comprises a semi-permeable layer positioned between a plenum 115 and a cell culture compartment 111, in accordance with some embodiments. Such a semi-permeable layer 113 may allow whole cells to pass through the plenum 115 of the device. Such a semi-permeable layer 113 may also allow certain types of cells, tissues, or small molecules (e.g., drugs) to pass through the barrier (e.g., from the plenum 115 to the cell culture compartment 111, or from the cell culture compartment 111 to the plenum 115, as indicated by the arrows in FIG. 3). The semi-permeable layer 113 may be configured to allow only plasma exchange between the plenum 115 and the cell culture compartment 111.

The cell culture compartment 111 may comprise on or more cell culture chambers, as described elsewhere herein. The cell culture compartment 111 may be located within the elastic cell culture device 104. The cell culture compartment 111 may be located externally with respect to the elastic cell culture device 104. The cell culture compartment 111 may be a structure that is not attached to the elastic cell culture device 104, but only connected via a channel or tubing. The cell culture compartment 111 may be a channel. The cell culture compartment 111 may be a well. The cell culture compartment 111 may be an enclosed space located within the elastic cell culture device 104. The cell culture compartment 111 may comprise one or more walls that define its geometry. The cell culture compartment 111 may be a trough. The cell culture compartment 111 may comprise a hydrogel. The cell culture compartment 111 may comprise a surface coating, as described elsewhere herein. The cell culture compartment 111 may be composed of a material that is suitable for microcopy imaging (e.g., a clear, translucent material).

The semi-permeable layer 113 may be a filter. The semi-permeable layer 113 may be a membrane, as described elsewhere herein. The semi-permeable layer 113 may comprise a synthetic material, as described elsewhere herein. The semi-permeable layer 113 may comprise a porous material or a microporous material, as described elsewhere herein.

The plasma-exchange animal-hip hybrid system 107 may comprise a first channel 117a and a second channel 117b, which may connect to a first blood vessel port 105a and a second blood vessel port 105b, and to the plasma exchange cell culture device 109, as shown in FIG. 3.

Figure 4:
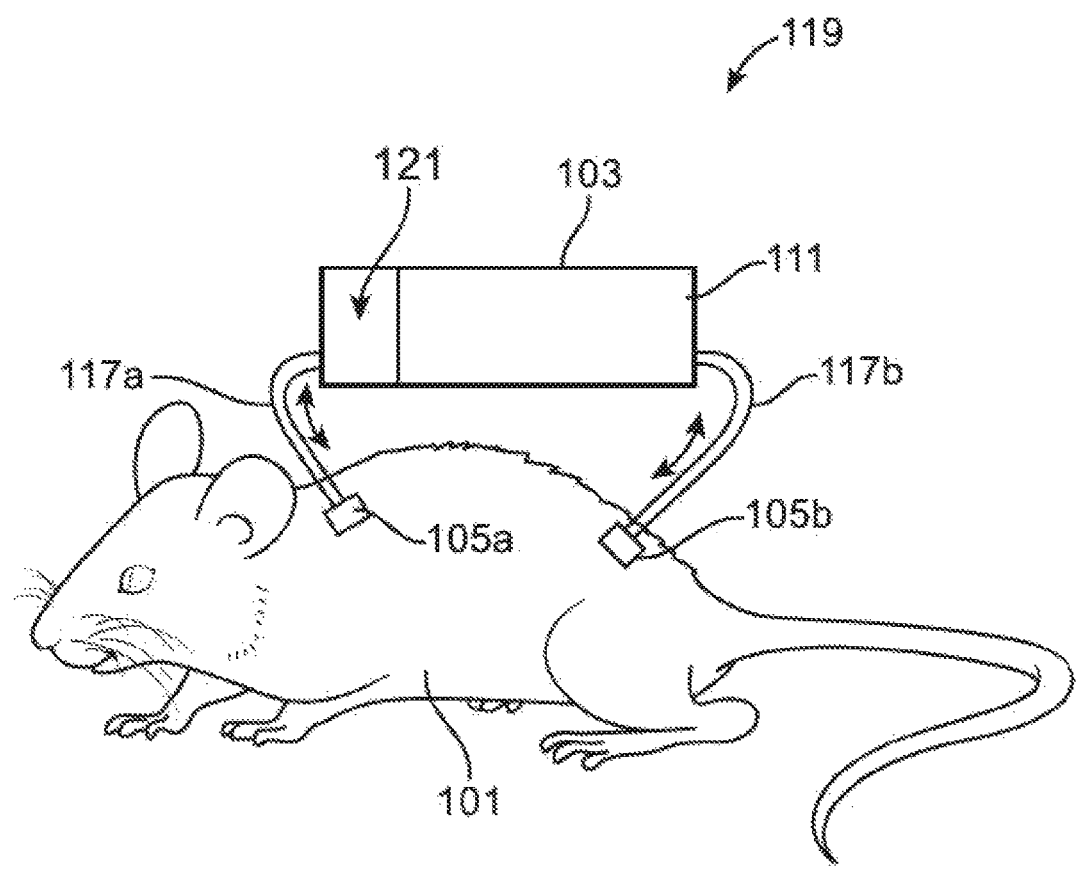
FIG. 4 illustrates an example of a pre-filtering animal-chip hybrid system comprising an animal subject and a cell culture device with a pre-filter (e.g., a microporous membrane or an epithelial cell layer) positioned between the fluid channel and a cell culture compartment, in accordance with some embodiments.

FIG. 4 illustrates an example of a pre-filtering animal-chip hybrid system 119 comprising an animal subject 101 and a cell culture device 103 with a pre-filter 121 (e.g., a semi-permeable membrane such as synthetic and/or a biologic membrane) positioned between a first channel 117a and a cell culture compartment 111, in accordance with some embodiments. Alternatively, the pre-filter 121 may be positioned between the cell culture compartment 111 and the second channel 117b. In another example, the pre-filtering animal-chip hybrid system 119 may comprise two or more pre-filters 121 that may be connected with each other in series or in parallel. In another example, a pre-filter 121 may be positioned between the first blood vessel port 105a and the first channel 117a. In this case, the pre-filter 121 may filter out any desired cell, tissue, and/or small molecule from the bloodstream of the animal subject 101 prior to entering the cell culture device 103. In yet another example, a pre-filter 121 may be positioned between the second channel 117b and the second blood vessel port 105b. In this case, the pre-filter 121 may filter out any desired cell, tissue, and/or small molecule from the flow output of then cell culture device 103 prior to entering the bloodstream of the animal subject 101. In another example, the first port and/or the second port (not shown in FIG. 4) of the cell culture device 103 and/or the first blood vessel port 105a and/or the second blood vessel port 105b may comprise one or more "Y" connectors that connect to one or more new lines (e.g., new channels or tubing). In this case, one or more pre-filters 121 may be positioned between the first port, the second port, the first blood vessel port 105a, and/or the second blood vessel port and any one of the new lines that are connected to any one of the "Y" connectors. For example, a pre-filter 121 may be positioned in between the second port of the cell culture device 103 and a "Y" connector. The "Y" connector may further connect to the second channel 117b and a new line (not shown in FIG. 4). The new line may be used to collect a filtered fluid sample that has been in contact with the cell culture compartment 111 but yet to be recirculated into the bloodstream of the animal subject 101.

The pre-filter 121 may be positioned to selectively allow only certain types of cells, tissues, or small molecules (e.g., drugs) to pass through the pre-filter 121 and enter the cell culture compartment 111 of the cell culture device 103, while blocking other types of cells, tissues, or small molecules (e.g., drugs) from passing through the pre-filter 121 and entering the cell culture compartment 111 of the cell culture device 103. Non-limiting examples of pre-filters include porous membranes, high surface-area convoluted membranes, and biological filters such as kidney cells or epithelial cells.

Figure 5:
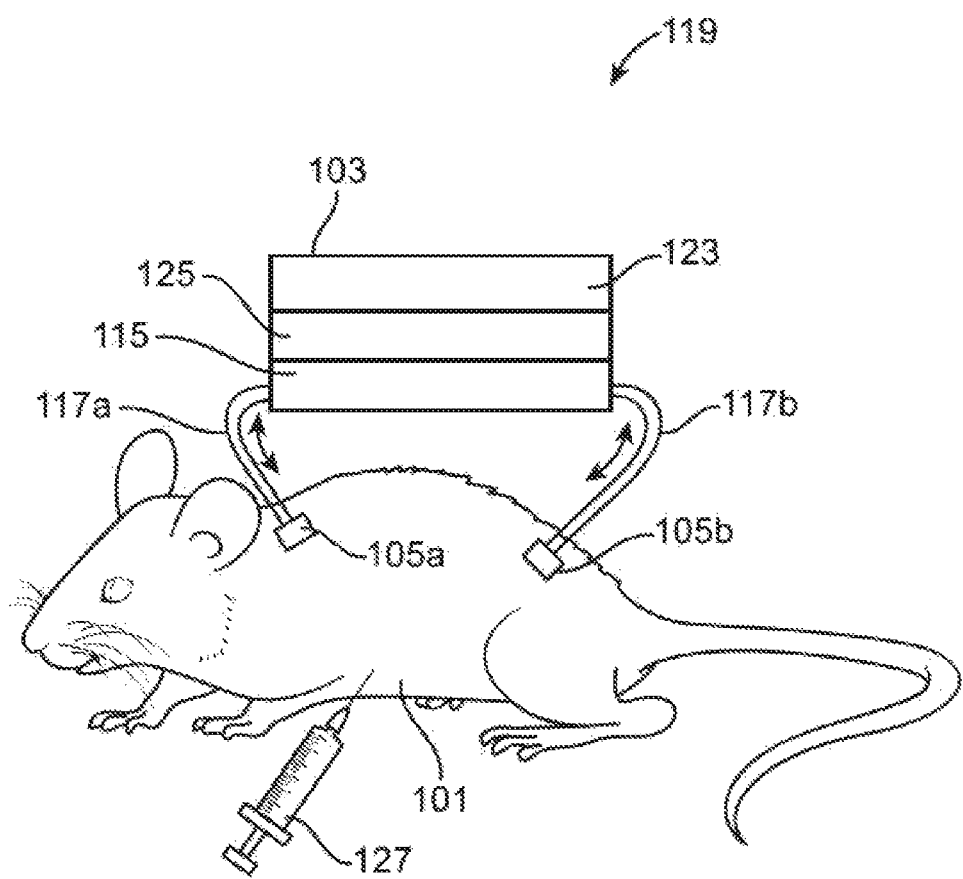
FIG. 5 illustrates an example of a pre-filtering animal-chip hybrid system comprising an animal subject and a cell culture device with an epithelial cell layer positioned between the plenum and a readout layer, in accordance with some embodiments.

FIG. 5 illustrates yet another example of a pre-filtering animal-chip hybrid system 119 comprising an animal subject 101 and a cell culture device 103 with a semi-permeable layer (i.e., an epithelial cell layer 125) positioned between a plenum 115 and a readout layer 123, in accordance with some embodiments. The plenum 115, the epithelial cell layer 125, and the readout layer 123 may be in fluid connection with each other. In some cases, the readout layer 123 is a cell culture compartment having a transparent or translucent portion to allow for detection by a detector. The epithelial cell layer 125 may selectively allow only certain types of cells, tissues, or small molecules (e.g., drugs) present in the plenum 115 of the cell culture device 103 to pass through the epithelial cell layer 125 and interact with the readout layer 123 of the cell culture device 103. The epithelial cell layer 125 may comprise blood brain barrier (BBB) epithelial cells. The epithelial cell layer 125 may comprise a substrate further comprising a first plurality of cells. The first plurality of cells may be epithelial cells. The first plurality of cells may be endothelial cells. The first plurality of cells may be deposited onto the substrate so as to form a layer.

The epithelial cell layer 125 may comprise a cell layer with a thickness of about 0.5 microns to about 20 microns. The epithelial cell layer 125 may comprise a cell layer with a thickness of at least about 0.5 microns. The epithelial cell layer 125 may comprise a cell layer with a thickness of at most about 20 microns. The epithelial cell layer 125 may comprise a cell layer with a thickness of about 0.5 microns to about 1 micron, about 0.5 microns to about 1.5 microns, about 0.5 microns to about 2 microns, about 0.5 microns to about 2.5 microns, about 0.5 microns to about 5 microns, about 0.5 microns to about 10 microns, about 0.5 microns to about 20 microns, about 1 micron to about 1.5 microns, about 1 micron to about 2 microns, about 1 micron to about 2.5 microns, about 1 micron to about 5 microns, about 1 micron to about 10 microns, about 1 micron to about 20 microns, about 1.5 microns to about 2 microns, about 1.5 microns to about 2.5 microns, about 1.5 microns to about 5 microns, about 1.5 microns to about 10 microns, about 1.5 microns to about 20 microns, about 2 microns to about 2.5 microns, about 2 microns to about 5 microns, about 2 microns to about 10 microns, about 2 microns to about 20 microns, about 2.5 microns to about 5 microns, about 2.5 microns to about 10 microns, about 2.5 microns to about 20 microns, about 5 microns to about 10 microns, about 5 microns to about 20 microns, or about 10 microns to about 20 microns. The epithelial cell layer 125 may comprise a cell layer with a thickness of about 0.5 microns, about 1 micron, about 1.5 microns, about 2 microns, about 2.5 microns, about 5 microns, about 10 microns, or about 20 microns.

The substrate of the epithelial cell layer 125 may comprise a plastic material, a glass material, a hydrogel material, an extracellular matrix material, or any other suitable material for the culture of cells.

The readout layer 123 of the cell culture device 103 may comprise a second plurality of cells. The second plurality of cells may be neurons or other brain cells such as, but not limited to glial cells, microglia, astrocytes, and oligodendrocytes. The readout layer 123 of the cell culture device 103 may comprise any other cell type. In some cases, one or more analytes 127 may be administered to the animal subject 101. In such cases, the effects of the analyte 127 on the second plurality of cells located in the readout layer 123 may be detected. In some embodiments, the readout layer 123 of the cell culture device 103 may comprise non-cell material introduced or incorporated to detectably change when exposed to certain analytes 127. In some cases, the readout layer 123 of the cell culture device 103 may comprise a detector configured to change readout values (e.g., numerical readout values) when the detector is exposed to certain analytes 127. In other cases, the readout layer 123 of the cell culture device 103 may comprise a detector configured to change readout values (e.g., numerical readout values) when cells in the readout layer 123 are exposed to certain analytes 127.

Figure 6:
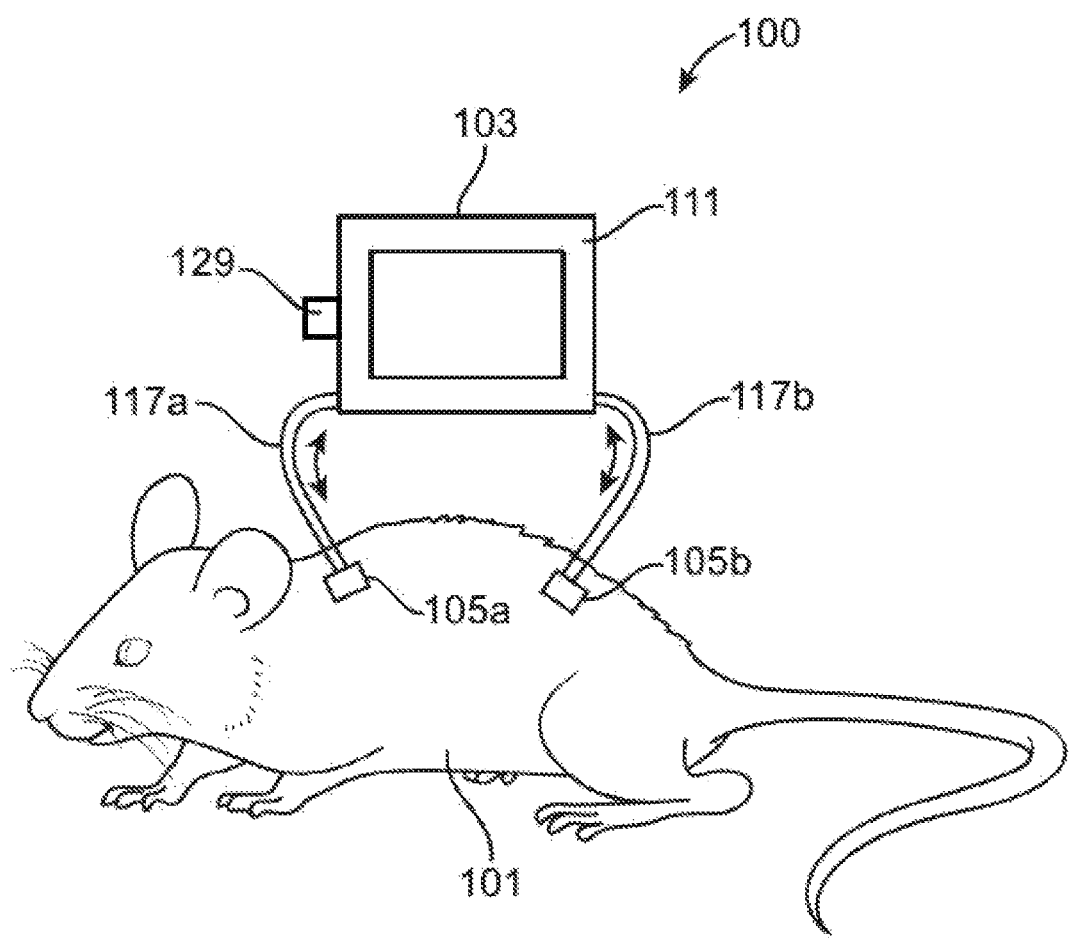
FIG. 6 illustrates an example of an animal-chip hybrid system comprising an animal subject and a cell culture device with a device port connected to a cell culture compartment (e.g., to introduce a drug for performing dosing experiments), in accordance with some embodiments.

FIG. 6 illustrates another example of an animal-chip hybrid system 100 comprising an animal subject 101 and a cell culture device 103 with a device port 129 connected to the cell culture compartment 111 (e.g., to introduce a drug for performing dosing experiments), in accordance with some embodiments. Such an animal-chip hybrid system 100 may be advantageous for performing drug dosing experiments, e.g., to test drugs that may be lethal to one organ of the animal subject because they are not yet optimized for toxicity levels.

Different drug treatments (with different doses of the same drug or doses of different drugs) may be administered to the cultured cells by entering the cell culture compartment 111 or the fluid channel (not shown in FIG. 6) of the cell culture device 103 through the device port 129.

The cell culture compartment 111 may have a volume of about 100 microliters (µl). The cell culture compartment 111 may have a volume of about 1 µl to about 10,000 µl. The cell compartment 111 may have a volume of at least about 1 µl. The cell culture compartment 111 may have a volume of at most about 10,000 µl. The cell culture compartment 111 may have a volume of about 1 µl to about 5 about 1 µl to about 10 µl, about 1 µl to about 25 µl, about 1 µl to about 50 µl, about 1 µl to about 100 µl, about 1 µl to about 250 µl, about 1 µl to about 500 µl, about 1 µl to about 1,000 µl, about 1 µl to about 5,000 µl, about 1 µl to about 10,000 µl, about 5 µl to about 10 µl, about 5 µl to about 25 µl, about 5 µl to about 50 µl, about 5 µl to about 100 µl, about 5 µl to about 250 µl, about 5 µl to about 500 µl, about 5 µl to about 1,000 µl, about 5 µl to about 5,000 µl, about 5 µl to about 10,000 µl, about 10 µl to about 25 µl, about 10 µl to about 50 µl, about 10 µl to about 100 µl, about 10 µl to about 250 µl, about 10 µl to about 500 µl, about 10 µl to about 1,000 µl, about 10 µl to about 5,000 µl, about 10 µl to about 10,000 µl, about 25 µl to about 50 µl, about 25 µl to about 100 µl, about 25 µl to about 250 µl, about 25 µl to about 500 µl, about 25 µl to about 1,000 µl, about 25 µl to about 5,000 µl, about 25 µl to about 10,000 about 50 µl to about 100 µl, about 50 µl to about 250 µl, about 50 µl to about 500 µl, about 50 µl to about 1,000 µl, about 50 µl to about 5,000 µl, about 50 µl to about 10,000 µl, about 100 µl to about 250 µl, about 100 µl to about 500 µl, about 100 µl to about 1,000 µl, about 100 µl to about 5,000 µl, about 100 µl to about 10,000 µl, about 250 µl to about 500 µl, about 250 µl to about 1,000 µl, about 250 µl to about 5,000 µl, about 250 µl to about 10,000 µl, about 500 µl to about 1,000 µl, about 500 µl to about 5,000 µl, about 500 µl to about 10,000 µl, about 1,000 µl to about 5,000 µl, about 1,000 µl to about 10,000 µl, or about 5,000 µl to about 10,000 µl. The cell culture compartment 111 may have a volume of about 1 µl, about 5 µl, about 10 µl, about 25 µl, about 50 µl, about 100 µl, about 250 µl, about 500 µl, about 1,000 µl, about 5,000 µl, or about 10,000 µl.

The animal-chip hybrid system 100 may be used to perform drug dosing experiments at a small scale or micro scale. For example, a microdose of a drug (e.g., a nanoliter amount of drug) may be used to perform the drug dosing experiment in the animal-chip hybrid system 100 instead of the normal amount of drug (e.g., a milliliter amount of drug) that may be used in a larger scale drug dosing experiment. This may be advantageous because the animal subject 101 is exposed to only a small dose of drug, such that the damage to the internal organs of the animal subject 101 is minimized or eliminated.

The cell culture device 103 may comprise a device port 129 in addition to a first port and a second port (not illustrated in FIGS. 1-9). Thus, the cell culture device 103 may comprise three ports or more. The device port 129 may be an injection port. The device port 129 may be a needle port. The device port 129 may be an opening on surface of the cell culture device 103 that may enable access to the interior of the cell culture device 103. The device port 129 may comprise a re-sealable septum that covers a portal of the device port 129. The device port 129 may comprise a re-sealable membrane that covers a portal of the device port 129. For example, a drug amount may be injected into the cell compartment 111 by inserting a syringe loaded with the drug, through a re-sealable septum at the opening of the device port 129, and into the cell compartment 111. The device port 129 may be configured to receive a stopper or a plug to seal the opening of the device port 129. For example, after an amount of drug is injected into the cell culture compartment 111, a stopper may be placed in the device port 129 in order to prevent fluid from exiting the cell culture device 103 and/or any airborne contaminant to enter the cell culture device 103 via the device port 129. The device port 129 may reversibly connect with a channel, tubing, a stopper, or a plug via a luer lock connector, a compression fitting, an adapter, a coupling, a quick connect hose fitting, a syringe, or any other suitable fitting. The device port 129 may comprise screw threads that enable a connection of the device port 129 to a channel, tubing, a stopper, a plug, or any combination thereof. The device port 129 may comprise a filter. The filter may comprise a pore size of about 0.1 microns (µm). The filter may comprise a pore size of about 0.20 microns (µm). The filter may comprise a pore size of about 0.22 microns (µm). The filter may comprise a pore size of about 0.45 microns (µm). The filter may comprise a pore size of about 0.80 microns (µm). The filter may be a syringe filter. The filter may be a disc filter. The filter may be positioned in between a channel (e.g., tubing) and the third device port 129.

Figure 7:
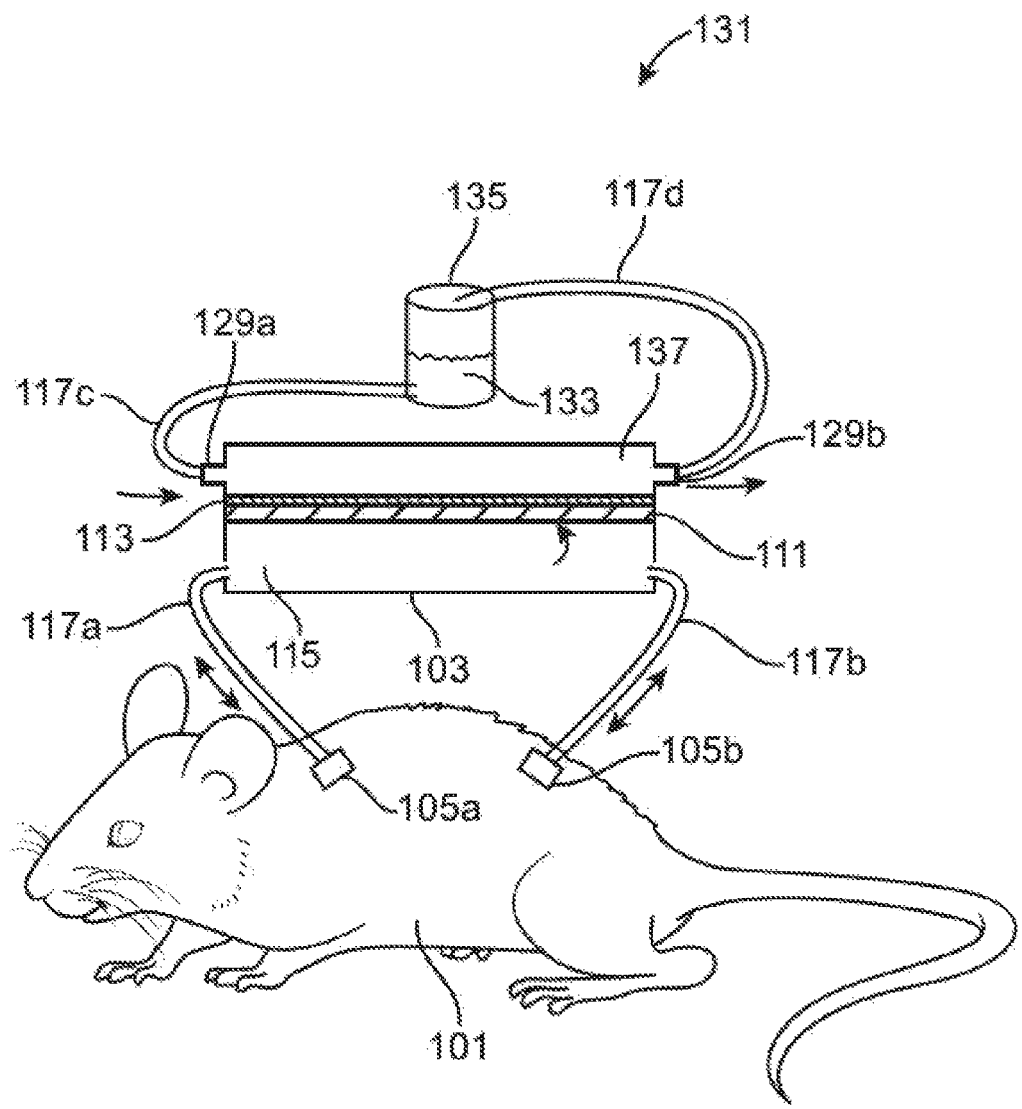
FIG. 7 illustrates an example of a multi-port animal-chip hybrid system comprising an animal subject and a cell culture device with a device port connected to a drug perfusion compartment (e.g., to introduce a drug for performing dosing experiments), a fourth port connected to the drug perfusion compartment (e.g., to exit a drug for performing dosing experiments), and a cell culture compartment separated from the drug perfusion compartment by a semi-permeable layer, in accordance with some embodiments.

FIG. 7 illustrates an example of a multi-port animal-chip hybrid system 131 comprising an animal subject 101 and a cell culture device 103 with a first device port 129a and a second device port 129b. The first device port 129a may be in fluid connection with a drug perfusion compartment 137 (e.g., to introduce a drug for performing dosing or toxicity experiments). In other words, the first device port 129a may be an inlet that is used for introducing a drug and/or any other suitable reagent into the cell culture device 103 and/or into the cell culture compartment 111. The second device port 129b may be in fluid connection with the drug perfusion compartment 137 (e.g., to remove a drug for performing dosing or toxicity experiments), in accordance with some embodiments. For example, the second device port 129b may be an outlet that is used for removing a drug 133 and/or any other suitable reagent from the cell culture device 103 and/or form the cell culture compartment 111. In this example, the drug perfusion compartment 137 is separated from a cell culture compartment 111 by a semi-permeable layer 113, as described herein. The semi-permeable layer 113 may be a porous barrier. This arrangement allows for testing the effects of different drugs on cells and/or tissue found in the cell culture compartment 111, or for recirculating a same drug 133.

Furthermore, the first device port 129a may be in fluid connection with a third channel 117c, as illustrated in FIG. 7. The third channel 117c may be in fluid connection with a drug reservoir 135 that contains a drug 133. The second device port 129b may be in fluid connection with a fourth channel 117*d*, as illustrated in FIG. 7. The fourth channel 117*d* may be in fluid connection with a drug reservoir 135 that contains a drug 133. In this example, the drug 133 flows from the reservoir 135, through the third channel 117*c*, through the first device port 129*a*, and into the drug perfusion compartment 137. In addition, the drug 133 may be removed from the drug perfusion compartment 137 by flushing and/or draining the drug 133 from the drug perfusion compartment 137, through the second device port 129*b*, into the fourth channel 117*d*, and into the drug reservoir 135, as shown in FIG. 7. In this manner, the flow of the drug 133 or any other fluid being introduced into the drug perfusion compartment 137 follows the direction of the arrows shown in FIG. 7 (i.e., where the first device port 129*a* serves as an inlet for the drug 133 and the second device port 129*b* serves as the outlet for the drug 133). The fluid flow from the plenum 115 and into the animal subject 101 follows the direction of flow as illustrated by the arrows in FIG. 7 and described elsewhere herein, where the first channel 117*a* serves as an inlet and the second channel 117*b* serves as an outlet.

The multi-port animal-chip hybrid system 131 may comprise a pump, one or more valves, one or more manifolds, and/or tubing to enable the flow of drug 133 from the reservoir 135 into the drug perfusion compartment 137. The pump may be an infusion pump, a peristatic pump, an electronic pump, a disposable pump, a positive displacement pump, an impulse pump, a velocity pump, a gravity pump, a steam pump, a valveless pump, or any combination thereof. The pump and/or the one or more valves may be controlled by the computing system provided herein.

Such a multi-port animal-chip hybrid system 131 may be advantageous for performing drug dosing experiments, e.g., to test drugs that may be lethal to one organ of the animal subject 101 because they are not yet optimized for toxicity levels. Different drug treatments (with different doses of the same drug or doses of different drugs) may be administered to the cultured cells and/or tissue by entering the drug perfusion compartment 137 of the cell culture device 103 through the first device port 129*a* and by exiting the drug perfusion compartment 137 of the cell culture device 103 through the second device port 129*b*. The multi-port animal-chip hybrid system 131 may be used to perform drug dosing experiments at a small scale or micro scale. For example, a microdose of a drug (e.g., a nanoliter amount of drug) may be introduced through the first device port 129*a* instead of a conventional amount of drug (e.g., a milliliter amount of drug) that may be used in a larger scale drug dosing experiment. This may be advantageous because the animal subject 101 is exposed to only a small dose of drug, such that the damage to the internal organs of the animal subject 101 is minimized or eliminated. In addition, since a drug may be recirculated through the drug perfusion compartment 137, significantly less of the drug may be needed to be tested on the cell and/or tissue in the cell culture compartment 111. This may be advantageous because the animal subject is exposed to only a small dose of drug, such that the damage to the internal organs of the animal subject is minimized or eliminated. In addition, this method allows for testing of drugs that are expensive or limited in supply.

The first device port 129*a* may allow for different combinations of one or more drugs to be serially administered. In addition, the second device port 129 may enable one or more drugs to be drained out and/or flushed out to purge the introduced one or more drugs from the cell culturing environment (i.e., from the cell culture compartment 111). A porous or semi-permeable membrane (e.g., a filter) may be placed between the plenum 115 of the cell culture device 103 and the drug perfusion compartment 137, such that very little drug enters the animal. In another example, a semi-permeable layer may be positioned between the plenum 115 and the cell culture compartment 111. In another case, the cell culture device 103 may comprise two semi-permeable layers. In this case, the first semi-permeable layer may be positioned between the drug perfusion compartment 137 and the cell culture compartment 111, as shown in FIG. 7, and additionally, the second semi-permeable layer may be positioned between the cell culture compartment 111 and the plenum 115.

The readout layer of the cell culture device 103 (e.g., a cell culture compartment 111) may comprise non-biological material (not shown in FIG. 7) built to detectably change (i.e., a physical and/or a chemical characteristic) when exposed to certain analytes. The readout layer of the cell culture device 103 may comprise a detector configured to change readout values (e.g., numerical readout values) when exposed to certain analytes. The readout may comprise a detector (not shown in FIG. 7) configured to measure one or more parameters associated with the cell culture compartment or the cells. The parameters may be selected from the group consisting of solution flow, temperature, morphology, color, fluorescence, luminescence, pH, and electrochemical properties. The detector may be a camera or a microscope. The detector may comprise a radio-frequency identification (RFID) transponder. The status of the detector is read by a camera unattached to the animal subject 101.

FIG. 8 illustrates an example of a multiplexed animal-chip hybrid system 139 comprising an animal subject 101 and a cell culture device 103 with a plurality of N separate cell culture compartments, in accordance with some embodiments. The multiplexed animal-chip hybrid system 139 may comprise a first cell culture compartment 111*a*, a second cell culture compartment 111*b*, a third cell culture compartment 111*c*, a fourth cell culture compartment 111*d*, a fifth cell culture compartment 111*e*, a sixth cell culture compartment 111*f*, a seventh cell culture compartment 111*g*, an eighth cell culture compartment 111*h*, a ninth cell culture compartment 111*i*, a tenth cell culture compartment 111*j*, an eleventh cell culture compartment 111*k*, and a twelfth cell culture compartment 111*l*.

The multiplexed animal-chip hybrid system 139 may comprise about 1 one cell culture compartment to about 25 cell culture compartments. The multiplexed animal-chip hybrid system 139 may comprise at least about 1 one cell culture compartment. The multiplexed animal-chip hybrid system 139 may comprise at most about 25 cell culture compartments. The multiplexed animal-chip hybrid system 139 may comprise about 1 one cell culture compartment to about 5 cell culture compartments, about 1 one cell culture compartment to about 10 cell culture compartments, about 1 one cell culture compartment to about 15 cell culture compartments, about 1 one cell culture compartment to about 20 cell culture compartments, about 1 one cell culture compartment to about 25 cell culture compartments, about 5 cell culture compartments to about 10 cell culture compartments, about 5 cell culture compartments to about 15 cell culture compartments, about 5 cell culture compartments to about 20 cell culture compartments, about 5 cell culture compartments to about 25 cell culture compartments, about 10 cell culture compartments to about 15 cell culture compartments, about 10 cell culture compartments to about 20 cell culture compartments, about 10 cell culture compartments to about 25 cell culture compartments, about 15 cell culture compartments to about 20 cell culture compartments, about 15 cell culture compartments to about 25 cell culture compartments, or about 20 cell culture compartments to about 25 cell culture compartments. The multiplexed animal-chip hybrid system 139 may comprise about 1 one cell culture compartment, about 5 cell culture compartments, about 10 cell culture compartments, about 15 cell culture compartments, about 20 cell culture compartments, or about 25 cell culture compartments.

The multiplexed animal-chip hybrid system 139 may comprise about 1 cell culture compartment to about 1,024 cell culture compartments. The multiplexed animal-chip hybrid system 139 may comprise at least about 1 cell culture compartment. The multiplexed animal-chip hybrid system 139 may comprise at most about 1,024 cell culture compartments. The multiplexed animal-chip hybrid system 139 may comprise about 1 cell culture compartment to about 2 cell culture compartments, about 1 cell culture compartment to about 4 cell culture compartments, about 1 cell culture compartment to about 8 cell culture compartments, about 1 cell culture compartment to about 16 cell culture compartments, about 1 cell culture compartment to about 32 cell culture compartments, about 1 cell culture compartment to about 64 cell culture compartments, about 1 cell culture compartment to about 128 cell culture compartments, about 1 cell culture compartment to about 256 cell culture compartments, about 1 cell culture compartment to about 512 cell culture compartments, about 1 cell culture compartment to about 1,024 cell culture compartments, about 2 cell culture compartments to about 4 cell culture compartments, about 2 cell culture compartments to about 8 cell culture compartments, about 2 cell culture compartments to about 16 cell culture compartments, about 2 cell culture compartments to about 32 cell culture compartments, about 2 cell culture compartments to about 64 cell culture compartments, about 2 cell culture compartments to about 128 cell culture compartments, about 2 cell culture compartments to about 256 cell culture compartments, about 2 cell culture compartments to about 512 cell culture compartments, about 2 cell culture compartments to about 1,024 cell culture compartments, about 4 cell culture compartments to about 8 cell culture compartments, about 4 cell culture compartments to about 16 cell culture compartments, about 4 cell culture compartments to about 32 cell culture compartments, about 4 cell culture compartments to about 64 cell culture compartments, about 4 cell culture compartments to about 128 cell culture compartments, about 4 cell culture compartments to about 256 cell culture compartments, about 4 cell culture compartments to about 512 cell culture compartments, about 4 cell culture compartments to about 1,024 cell culture compartments, about 8 cell culture compartments to about 16 cell culture compartments, about 8 cell culture compartments to about 32 cell culture compartments, about 8 cell culture compartments to about 64 cell culture compartments, about 8 cell culture compartments to about 128 cell culture compartments, about 8 cell culture compartments to about 256 cell culture compartments, about 8 cell culture compartments to about 512 cell culture compartments, about 8 cell culture compartments to about 1,024 cell culture compartments, about 16 cell culture compartments to about 32 cell culture compartments, about 16 cell culture compartments to about 64 cell culture compartments, about 16 cell culture compartments to about 128 cell culture compartments, about 16 cell culture compartments to about 256 cell culture compartments, about 16 cell culture compartments to about 512 cell culture compartments, about 16 cell culture compartments to about 1,024 cell culture compartments, about 32 cell culture compartments to about 64 cell culture compartments, about 32 cell culture compartments to about 128 cell culture compartments, about 32 cell culture compartments to about 256 cell culture compartments, about 32 cell culture compartments to about 512 cell culture compartments, about 32 cell culture compartments to about 1,024 cell culture compartments, about 64 cell culture compartments to about 128 cell culture compartments, about 64 cell culture compartments to about 256 cell culture compartments, about 64 cell culture compartments to about 512 cell culture compartments, about 64 cell culture compartments to about 1,024 cell culture compartments, about 128 cell culture compartments to about 256 cell culture compartments, about 128 cell culture compartments to about 512 cell culture compartments, about 128 cell culture compartments to about 1,024 cell culture compartments, about 256 cell culture compartments to about 512 cell culture compartments, about 256 cell culture compartments to about 1,024 cell culture compartments, or about 512 cell culture compartments to about 1,024 cell culture compartments. The multiplexed animal-chip hybrid system 139 may comprise about 1 cell culture compartment, about 2 cell culture compartments, about 4 cell culture compartments, about 8 cell culture compartments, about 16 cell culture compartments, about 32 cell culture compartments, about 64 cell culture compartments, about 128 cell culture compartments, about 256 cell culture compartments, about 512 cell culture compartments, or about 1,024 cell culture compartments.

Such a multiplexed animal-chip hybrid system 139 may be advantageous for simultaneously performing multiple cell culture operations or experiments under similar or different experimental conditions.

For example, the plurality of N separate cell culture compartments may be placed in a rectangular array format, where each position of the rectangular array comprises a separate cell culture compartment (e.g., to perform experiments under different conditions, or to perform a different replicate of an experiment under the same conditions). For example, each separate experiment may comprise cells deposited into a cell culture compartment from a different source (e.g., a xenograft experiment from different patients). As another example, each separate experiment may comprise a different tissue type from the same subject (e.g., lung, heart, etc.). As another example, each separate experiment may comprise a different small or large molecule (e.g., drug or antibody). As another example, each separate experiment may comprise a different dosing of a small or large molecule (e.g., drug or antibody). Having more than one cell culture compartments in the system may improve the signal to noise ratio of the results of experiment replicates. In other words, having more than one cell culture compartments in the system may decrease variance due to differences (e.g., physical and/or chemical) between cell culture compartments. In some examples, the variance may decrease due to averaging, whereas a true signal may be held constant across one or more cell culture compartments and survive averaging.

As another example, each separate experiment may comprise one of a plurality of replicate experiments under similar conditions as those of other separate cell culture compartments. In a preferred embodiment, the cell culture compartments are separated from the fluid channel by at least one semi-permeable layer. In one example, each separate experiment may comprise the same semi-permeable layer. As another example, each separate experiment may comprise a different semi-permeable layer. As another example, each separate experiment may comprise a different pre-filter. As another example, each separate experiment may comprise a different analyte or mixture of analytes.

As another example, replicate experiments could be performed using a plurality of identical multiplexed animal-chip hybrid systems 139, such that replicates of the same experiment (e.g., with identical experimental conditions) may be performed in different positions on the multiplexed animal-chip hybrid system 139 (e.g., a given position such as row and position of an rectangular array of separate cell culture chambers), to average out or eliminate position-dependent effects. As another example, each separate experiment may comprise cells and/or tissue having different human genotype canonical for a certain drug response (e.g., receptor selectivity variants, etc.) in order to assess a drug for a patient cross section. In some embodiments, each of the plurality of separate cell culture compartments contains cells and/or tissues from a variety of different organs. In some embodiments, each of the plurality of separate cell culture compartments contains cells and/or tissues from a variety of different human subjects.

Figure 9:
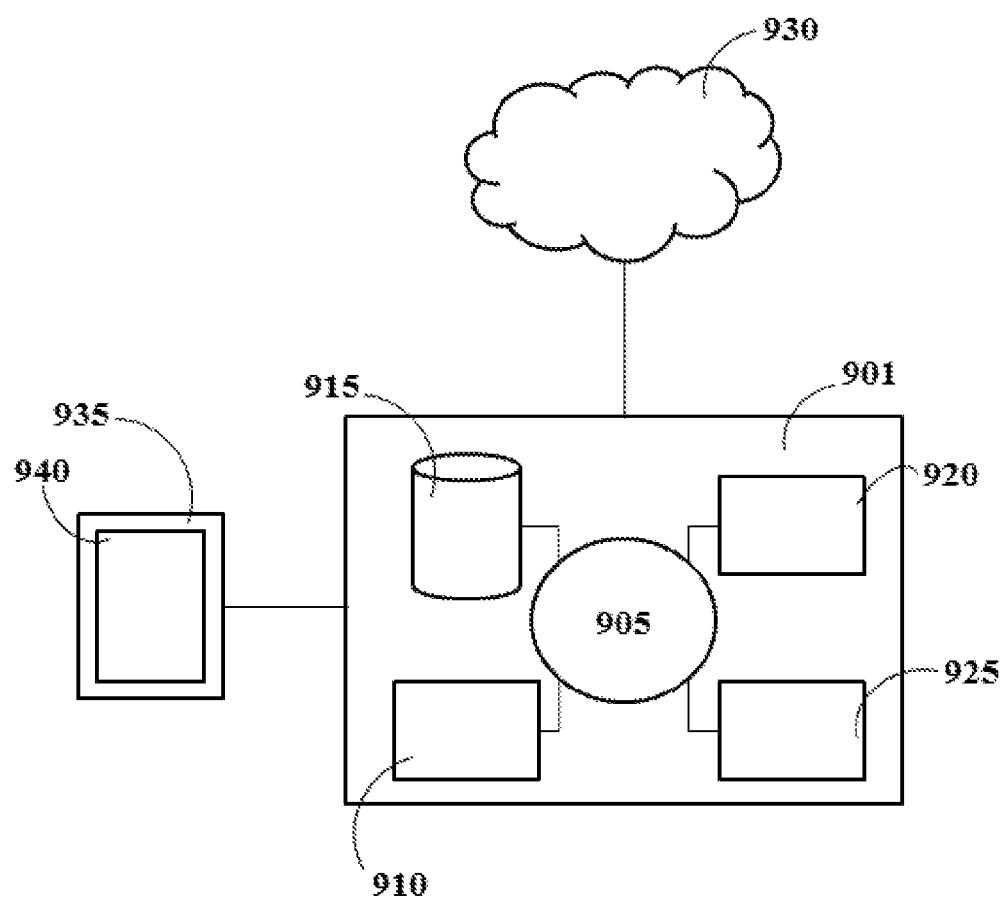
FIG. 9 illustrates a computer control system that is programmed or otherwise configured to implement methods provided herein.

FIG. 9 illustrates a computer control system that is programmed or otherwise configured to implement methods provided herein.

Computer Systems

The present disclosure provides computer systems that are programmed to implement methods of the disclosure. FIG. 9 shows a computer system 901 that is programmed or otherwise configured to (i) operate the detector (e.g., camera, microscope, or RFID transponder), (ii) measure one or more parameters associated with the cell culture compartment or the cells, (iii) read the status of the detector, (iv) operate the fluid flow systems of the cell culture device 103, and/or (v) display and/or save the one or more measured parameters associated with the cell culture compartment or the cells. The computer system 901 can regulate various aspects of analysis, calculation, and generation of the present disclosure, such as, for example, (i) operation of the detector (e.g., camera, microscope, or RFID transponder), (ii) measurement of one or more parameters associated with the cell culture compartment or the cells, (iii) reading the status of the detector, and/or (iv) displaying and/or saving the one or more measured parameters associated with the cell culture compartment or the cells. The computer system 901 can be an electronic device of a user or a computer system that is remotely located with respect to the electronic device. The electronic device can be a mobile electronic device (e.g., mobile telephone, smartphone, or portable computer).

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure (e.g., adjust perfusion flow, administer a drug, and/or detect a cell culture readout layer). Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., (i) to operate the detector (e.g., camera, microscope, or RFID transponder), (ii) to measure one or more parameters associated with the cell culture compartment or the cells, (iii) to read the status of the detector, and/or (iv) to display and/or to save the one or more measured parameters associated with the cell culture compartment or the cells). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930. In some cases, a user may remotely control and monitor experiments using the cell culture devices described herein.

In other embodiments, methods as described herein can be implemented by way of machine (e.g., computer processor) executable code stored on an electronic storage location of the computer system 901, such as, for example, on the memory 910 or electronic storage unit 915. In some cases, implementation by way of machine allows for automation of experiments (e.g., adjust perfusion flow, administer a drug, and/or detect a cell culture readout layer) using the cell culture devices described herein with limited need for user monitoring or guidance. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the devices, systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, (i) operation of the detector (e.g., camera, microscope, or RFID transponder), (ii) measurement of one or more parameters associated with the cell culture compartment or the cells, (iii) reading the status of the detector, or (iv) displaying the one or more measured parameters associated with the cell culture compartment or the cells. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, (i) operate the detector (e.g., camera, microscope, or RFID transponder), (ii) measure one or more parameters associated with the cell culture compartment or the cells, (iii) read the status of the detector, (iv) operate the fluid flow systems of the cell culture device 103, and/or (v) display the one or more measured parameters associated with the cell culture compartment or the cells.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Additional Embodiments

In an aspect, disclosed herein is a cell culture device comprising a fluid channel portion having a first port at a first end and a second port at a second end, and a first compartment for culturing cells, wherein a continuous or intermittent perfusion of blood from an animal subject enters the device at the first port and exits the device at the second port.

In some embodiments, the fluid channel portion and the first compartment are fluidly connected. In some embodiments, the device comprises a semi-permeable layer. In some embodiments, the semi-permeable layer is positioned between the first port and the first compartment. In some embodiments, an epithelial cell layer is positioned between the semi-permeable layer and the first compartment.

In some embodiments, the animal subject is a rodent or a primate. In some embodiments, the first port and the second port are connected to a continuous animal infusion system. In some embodiments, an epithelial cell layer is positioned between the fluid channel portion and the first compartment. In some embodiments, the device is mechanically attached to the animal subject.

In some embodiments, the device is elastic. In some embodiments, the device is comprised of polydimethylsiloxane (PDMS).

In some embodiments, the first compartment comprises a plurality of separate cell culture chambers. In some embodiments, each of the plurality of separate cell culture chambers contain tissues from a variety of different organs. In some embodiments, each of the plurality of separate cell culture chambers contain tissues from a variety of different human subjects.

In some embodiments, the device comprises a device port. In some embodiments, the device port is connected to the first compartment. In some embodiments, the device comprises a second compartment. In some embodiments, the first compartment and the second compartment are fluidly connected. In some embodiments, the second compartment comprises a device port. In some embodiments, a semi-permeable layer is positioned between the first compartment and the second compartment.

In some embodiments, the first compartment comprises cells. In some embodiments, the first compartment comprises cells from a source other than the animal subject. In some embodiments, the first compartment comprises cells from an animal that is younger or older than the animal subject. In some embodiments, the first compartment comprises a xenograft. In some embodiments, the first compartment comprises human cells.

In some embodiments, a system comprises the device and a detector, wherein the first compartment comprises cells, and wherein the detector measures one or more parameters associated with the first compartment or the cells. In some embodiments, the parameters are selected from the group consisting of solution flow, temperature, morphology, color, fluorescence, luminescence, pH, and electrochemical properties. In some embodiments, the detector is a camera or a microscope. In some embodiments, the detector comprises a radio-frequency identification (RFID) transponder. In some embodiments, the status of the detector is read by a camera unattached to the animal subject.

In another aspect, disclosed herein is a method for cell culture comprising: i) depositing cells into a first compartment of a cell culture device comprising a fluid channel portion having a first port at a first end and a second port at a second end; and ii) perfusing blood from an animal subject into the cell culture device, wherein the blood enters the device at the first port and exits the device at the second port, and wherein the perfusing is continuous or intermittent.

In some embodiments, the fluid channel portion and the first compartment are fluidly connected. In some embodiments, the device comprises a semi-permeable layer. In some embodiments, the semi-permeable layer is positioned between the first port and the first compartment. In some embodiments, the semi-permeable layer is positioned between the fluid channel portion and the first compartment. In some embodiments, the first port and the second port are connected to a continuous animal infusion system. In some embodiments, the animal subject is a rodent or a primate. In some embodiments, the first compartment comprises cells. In some embodiments, the first compartment comprises cells from a source other than the animal subject. In some embodiments, the first compartment comprises human cells.

EXAMPLES

Example 1—Testing Senescent Cells in a Young Mouse

A "plasma-exchange" animal-chip hybrid system is provided. The animal-chip hybrid system comprises a young mouse as the animal subject and a cell culture device with a semi-permeable layer positioned between the fluid channel and the cell culture compartment, as shown in FIG. 3. A collection of hepatocytes from another mouse that is older than the young mouse is introduced into the cell culture compartment. The semi-permeable layer does not allow immune cells to pass through the layer; therefore, the young mouse's immune system will not recognize the older mouse's cells in the cell culture compartment. The young mouse's blood is continuously perfused through the cell culture compartment and allowed to interact with the older mouse's cells in the cell culture compartment. Different experiments are run to culture hepatocytes for a period of one week, two weeks, one months, two months, and six months. At the end of the culturing periods, the physiological function of each cell culture is analyzed using standard techniques. Thus, the "plasma-exchange" animal-chip hybrid system enables experiments to test the effect of young mouse blood on older mouse cells.

Example 2—Culturing Neurons

A pre-filtering animal-chip hybrid system is provided. The animal-chip hybrid system comprises a primate as the animal subject and a cell culture device with an epithelial cell layer positioned between the fluid channel and a readout layer, as shown in FIG. 5. Human neurons derived from an Alzheimer's disease patient are introduced into the cell culture compartment (e.g., readout layer) of a cell culture device attached to a relatively young primate subject. The neurons are cultured in the readout layer in different experiments for a period of period of one week, two weeks, one months, two months, six months, and one year. During the cell culture of the neurons, the morphology of the neuron cells is intermittently measured (using a microscope). In some experiments, the cultured neurons are analyzed and the amount of amyloid precursor protein (APP) is determined at various time points. Thus, the animal-chip hybrid system enables experiments that test the effect of cell environment on neurons derived from an Alzheimer's disease patient.

Example 3—Culturing Xenografts

A multiplexed animal-chip hybrid system is provided. The animal-chip hybrid system comprises an animal subject and a cell culture device with a plurality of N separate cell culture chambers, as shown in FIG. 8. Such a multiplexed animal-chip hybrid system may be advantageous for simultaneously performing multiple cell culture operations or experiments under similar experimental conditions. The plurality of N separate cell culture chambers is placed in a rectangular array format, where each position of the rectangular array comprises a separate cell culture chamber, to perform multiple experiments under the same condition. Each of the plurality of N separate cell culture chambers comprises cells from a different xenograft from a human breast tumor. A drug candidate for blocking proliferation of human breast cancer cells is infused into the N separate cell culture chambers to test the effects of a treatment on the different xenograft cells. The drug is infused periodically and the xenografts are monitored over time. Thus, the animal-chip hybrid system enables multiplexed cell culture experiments to be performed to analyze the effect of a drug on the proliferation of xenografts obtained from human patients.

What is claimed is:

1. A method for processing or analyzing biological material, the method comprising:
providing a hybrid in vitro-in vivo cell culture device comprising a housing that includes a drug perfusion compartment separated from a cell culture compartment by a semi-permeable layer, a plenum separated from the cell culture compartment by an additional semi-permeable layer, the plenum comprising a channel having an inlet and an outlet;
attaching the housing to a body of a subject to perfuse the channel of the hybrid in vitro-in vivo cell culture device with bodily fluids of the subject through the inlet of the channel, such that the channel is in fluid communication with a circulatory system of the subject and the bodily fluids of the subject flows through the inlet of the channel to the plenum first;
attaching a drug reservoir to the hybrid in vitro-in vivo cell culture device by:
connecting an inlet channel of the drug reservoir to a first device port such that the first device port is in fluid communication with a drug of the drug reservoir and the first device port introduces a portion of the drug into the drug perfusion compartment; and
connecting an outlet channel of the drug reservoir to a second device port such that the second device port is in fluid communication with the drug reservoir and the second device port removes the portion of the drug from the hybrid in vitro-in vivo cell culture device; and
perfusing the drug perfusion compartment with the portion of the drug from the drug reservoir, the drug perfusion compartment separated from the cell culture compartment by the semi-permeable layer, such that a portion of the drug from the drug perfusion compartment passes through the semi-permeable layer to interact with one or more cells of the bodily fluids in the cell culture compartment.

2. The method of claim 1, wherein attaching the drug reservoir to the hybrid in vitro-in vivo cell culture device comprises establishing a fluid flow of the drug being introduced into the drug perfusion compartment such that the drug flows through the inlet channel to the drug perfusion compartment and through the outlet channel back to the drug reservoir.

3. The method of claim 1, wherein attaching the housing to the body of the subject to perfuse the channel of the hybrid in vitro-in vivo cell culture device with bodily fluids of the subject comprises:
attaching a first blood vessel port to the subject to allow the bodily fluids to exit out of a blood vessel of the subject;
attaching a second blood vessel port to the subject to allow the bodily fluids and additional fluids to enter the subject.

4. The method of claim 3, wherein providing the cell culture compartment with the first device port and the second device port further comprises:
connecting the inlet of the plenum to the first blood vessel port; and
connecting the outlet channel of the plenum to the second blood vessel port.

5. The method of claim 1, wherein perfusing the drug perfusion compartment with the drug from the drug reservoir further comprises utilizing a pump to control, via an intelligent computer system, an amount of the drug to perfuse the drug perfusion compartment.

6. The method of claim 1, wherein perfusing the drug perfusion compartment with the portion of the drug from the drug reservoir further comprises:
introducing a micro dose amount of the drug from the drug reservoir into the drug perfusion compartment; and
allowing a portion of the micro dose amount of the drug from the drug perfusion compartment to pass through the semi-permeable layer to interact with the one or more cells of the bodily fluids in the cell culture compartment.

7. The method of claim 6, further comprising recirculating the micro dose amount of the drug introduced into the drug perfusion compartment back to the drug reservoir.

8. The method of claim 1, wherein providing the housing that includes a semi-permeable layer further comprises providing the semi-permeable layer as at least one of a cell selective layer and a size selective layer.

9. The method of claim 1, wherein providing the housing further comprises:
inserting additional cells from an additional subject into the cell culture compartment of the housing; and
perfusing a portion of the bodily fluids of the subject to interact with the additional cells from the additional subject in the cell culture compartment.

10. The method of claim 9, wherein attaching the housing to the body of the subject further comprises causing the drug reservoir to administer predetermined doses to the subject at a series of predetermined time points.

11. A device for processing or analyzing biological material, the device comprising:
a hybrid in vitro-in vivo cell culture device comprising a housing that includes a drug perfusion compartment separated from a cell culture compartment by a semi-permeable layer, a plenum separated from the cell culture compartment by an additional semi-permeable layer, the plenum comprising a channel having an inlet and an outlet;
wherein the housing, when attached to a body of a subject, is operable to perfuse the channel of the hybrid in vitro-in vivo cell culture device with bodily fluids of the subject through the inlet of the channel, such that the channel is in fluid communication with a circulatory system of the subject and the bodily fluids of the subject flows through the inlet of the channel to the plenum first;
wherein a drug reservoir when attached to the hybrid in vitro-in vivo cell culture device by an inlet channel of the drug reservoir connected to a first device port in fluid communication with a drug of the drug reservoir is operable to introduce a portion of the drug into the drug perfusion compartment;
wherein the drug reservoir when attached to the hybrid in vitro-in vivo cell culture device by an outlet channel of the drug reservoir connected to a second device port in fluid communication with the drug reservoir is operable to remove the portion of the drug from the hybrid in vitro-in vivo cell culture device; and
wherein the drug perfusion compartment is separated from the cell culture compartment by the semi-permeable layer, such that when the drug perfusion compartment is perfused with the drug from the drug reservoir, the portion of the drug from the drug perfusion compartment passes through the semi-permeable layer to interact with one or more cells of the bodily fluids in the cell culture compartment.

12. The device of claim 11, wherein the drug reservoir further comprises an established fluid flow of the drug being introduced into the drug perfusion compartment such that the drug flows through the inlet channel to the drug perfusion compartment and through the outlet channel back to the drug reservoir.

13. The device of claim 11, wherein the housing, when attached to the body of the subject comprises:
   a first blood vessel port attached to the subject to allow the bodily fluids to exit out of a blood vessel of the subject; and
   a second blood vessel port attached to the subject to allow the bodily fluids and additional fluids to enter the subject.

14. The device of claim 13, wherein the cell culture compartment with the first device port and the second device port further comprises:
   the inlet of the plenum connected to the first blood vessel port; and
   the outlet of the plenum connected to the second blood vessel port.

15. The device of claim 11, wherein the drug perfusion compartment further comprises a pump, operable to control an amount of the drug to perfuse the drug perfusion compartment.

16. The device of claim 11, wherein the drug perfusion compartment and the drug reservoir are connected such that upon introducing a micro dose amount of the drug from the drug reservoir into the drug perfusion compartment the portion of the micro dose amount passes from the drug perfusion compartment through the semi-permeable layer to interact with the one or more cells of the bodily fluids in the cell culture compartment.

17. The device of claim 16, wherein the drug perfusion compartment is operable to recirculate the micro dose amount back to the drug reservoir.

18. The device of claim 11, wherein the semi-permeable layer comprises at least one of a cell selective layer and a size selective layer.

19. The device of claim 11, wherein the housing further comprises additional cells from an additional subject in the cell culture compartment of the housing, such that a portion of the bodily fluids of the subject interact with the additional cells from the additional subject in the cell culture compartment.

20. The device of claim 19, wherein the housing and the drug reservoir are connected such that the drug reservoir administers predetermined doses to the subject at a series of predetermined time points.

* * * * *